United States Patent
Nanko

(10) Patent No.: US 11,905,365 B2
(45) Date of Patent: Feb. 20, 2024

(54) FLUORINE-CONTAINING ETHER COMPOUND, LUBRICANT FOR MAGNETIC RECORDING MEDIUM, AND MAGNETIC RECORDING MEDIUM

(71) Applicant: Resonac Corporation, Tokyo (JP)

(72) Inventor: Masaki Nanko, Ichihara (JP)

(73) Assignee: Resonac Corporation, Tokyo (JP)

( * ) Notice: Subject to any disclaimer, the term of this patent is extended or adjusted under 35 U.S.C. 154(b) by 0 days.

(21) Appl. No.: 17/788,075

(22) PCT Filed: Dec. 22, 2020

(86) PCT No.: PCT/JP2020/047987
§ 371 (c)(1),
(2) Date: Jun. 22, 2022

(87) PCT Pub. No.: WO2021/132252
PCT Pub. Date: Jul. 1, 2021

(65) Prior Publication Data
US 2023/0090239 A1    Mar. 23, 2023

(30) Foreign Application Priority Data

Dec. 26, 2019 (JP) ................. 2019-236885

(51) Int. Cl.
*C08G 65/00* (2006.01)
*G11B 5/725* (2006.01)
(Continued)

(52) U.S. Cl.
CPC ....... *C08G 65/007* (2013.01); *C08G 65/3312* (2013.01); *C08G 65/33306* (2013.01);
(Continued)

(58) Field of Classification Search
CPC ..... G11B 5/7259; G11B 5/7257; G11B 5/725; C08G 65/007; C08G 65/33306;
(Continued)

(56) References Cited

U.S. PATENT DOCUMENTS 4,360,645 A    11/1982   Krespan et al.
4,526,833 A    7/1985    Burguette et al.
(Continued)

FOREIGN PATENT DOCUMENTS

CN    1705698 A    12/2005
CN    101121908 A    2/2008
(Continued)

OTHER PUBLICATIONS

Waltman ("Z-Tetraol composition and bonding to the underlying carbon surface", Journal of Colloid and Interface Science 333 (2009) 540-547). (Year: 2009).*

(Continued)

*Primary Examiner* — Holly Rickman
(74) *Attorney, Agent, or Firm* — Sughrue Mion, PLLC

(57) ABSTRACT

The present invention provides a fluorine-containing ether compound represented by the following formula:

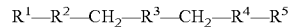

(in the formula, $R^3$ represents a perfluoropolyether chain; $R^1$ and $R^5$ each independently represent any of an alkyl group which may have a substituent, an organic group having a double bond or a triple bond, and a hydrogen atom; —$R^2$—$CH_2$—$R^3$— is represented by -[A]-[B]—O—$CH_2$—$R^3$; $R^3$—$CH_2$—$R^4$— is represented by $R^3$—$CH_2$—O—[C]-[D]-; [A] is represented by Formula (4), [B] is represented by Formula (5), [C] is represented by Formula (6), and [D] is represented by Formula (7)):

(Continued)

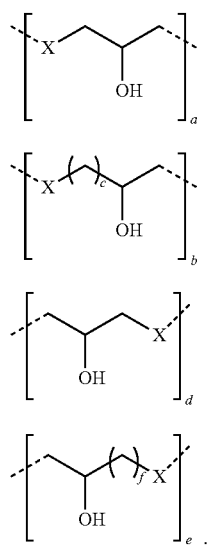

15 Claims, 1 Drawing Sheet

(51) Int. Cl.
 C08G 65/331 (2006.01)
 C08G 65/333 (2006.01)
 C10M 107/38 (2006.01)
 C10N 50/00 (2006.01)
 C10N 40/18 (2006.01)
 C10N 70/00 (2006.01)
(52) U.S. Cl.
 CPC ......... C10M 107/38 (2013.01); G11B 5/7257 (2020.08); C10M 2213/043 (2013.01); C10N 2040/18 (2013.01); C10N 2050/025 (2020.05); C10N 2070/00 (2013.01)
(58) Field of Classification Search
 CPC ............ C08G 65/3312; C10M 107/38; C10M 2213/043; C10M 2217/0206; C10N 2070/00; C10N 2050/025; C10N 2040/18
 See application file for complete search history.

(56) References Cited

U.S. PATENT DOCUMENTS

| | | | |
|---|---|---|---|
| 5,157,066 A | 10/1992 | Shoji et al. |
| 5,221,494 A | 6/1993 | Ikeda et al. |
| 5,604,032 A | 2/1997 | Kai et al. |
| 5,959,058 A | 9/1999 | Tonelli et al. |
| 6,323,163 B1 | 11/2001 | Sasaki et al. |
| 10,803,898 B2 | 10/2020 | Fukumoto et al. |
| 11,011,200 B2 | 5/2021 | Uetake et al. |
| 11,220,649 B2 | 1/2022 | Fukumoto et al. |
| 11,225,624 B2 | 1/2022 | Kato et al. |
| 11,261,394 B2 | 3/2022 | Kato et al. |
| 11,279,664 B2 | 3/2022 | Yagyu et al. |
| 11,427,779 B2 | 8/2022 | Yamaguchi et al. |
| 11,639,330 B2 | 5/2023 | Nanko et al. |
| 2004/0235685 A1 | 11/2004 | Russo et al. |
| 2005/0123855 A1 | 6/2005 | Hegel |
| 2006/0111251 A1 | 5/2006 | Tonelli et al. |
| 2009/0281250 A1 | 11/2009 | Desimone et al. |
| 2010/0233513 A1 | 9/2010 | Imai et al. |
| 2010/0261039 A1 | 10/2010 | Itoh et al. |
| 2012/0008228 A1 | 1/2012 | Mabuchi et al. |
| 2012/0225217 A1 | 9/2012 | Itoh et al. |
| 2012/0231297 A1 | 9/2012 | Sugiura et al. |
| 2013/0209837 A1 | 8/2013 | Sagata et al. |
| 2015/0274960 A1 | 10/2015 | Fukuda et al. |
| 2015/0371672 A1 | 12/2015 | Sagata |
| 2016/0068778 A1 | 3/2016 | Conley et al. |
| 2016/0203839 A1 | 7/2016 | Shimizu |
| 2017/0152456 A1 | 6/2017 | Sagata et al. |
| 2017/0260472 A1 | 9/2017 | Sagata et al. |
| 2017/0331155 A1 | 11/2017 | Yang et al. |
| 2018/0009773 A1 | 1/2018 | Uetake et al. |
| 2018/0022851 A1 | 1/2018 | Takao et al. |
| 2018/0047419 A1 | 2/2018 | Fukumoto et al. |
| 2018/0127543 A1 | 5/2018 | Watanabe et al. |
| 2019/0084911 A1 | 3/2019 | Yagyu et al. |
| 2019/0185621 A1 | 6/2019 | Naitou et al. |
| 2019/0352573 A1 | 11/2019 | Hatta et al. |
| 2019/0382675 A1 | 12/2019 | Fukumoto et al. |
| 2019/0382676 A1 | 12/2019 | Yamaguchi et al. |
| 2020/0010619 A1 | 1/2020 | Minami et al. |
| 2021/0062101 A1 | 3/2021 | Kato et al. |
| 2021/0062102 A1 | 3/2021 | Kato et al. |
| 2021/0155751 A1* | 5/2021 | Kato .................. C07C 233/25 |
| 2021/0188766 A1 | 6/2021 | Nanko et al. |
| 2022/0169941 A1 | 6/2022 | Shibata et al. |
| 2022/0372390 A1 | 11/2022 | Asano |
| 2023/0090239 A1 | 3/2023 | Nanko |

FOREIGN PATENT DOCUMENTS

| | | |
|---|---|---|
| CN | 102639477 A | 8/2012 |
| CN | 107849235 A | 3/2018 |
| CN | 114341094 A | 4/2022 |
| CN | 114599631 A | 6/2022 |
| EP | 1 479 753 A2 | 11/2004 |
| EP | 3 081 549 A1 | 10/2016 |
| JP | 57-176973 A | 10/1982 |
| JP | 61-126052 A | 6/1986 |
| JP | 3-7798 A | 1/1991 |
| JP | 5-12655 A | 1/1993 |
| JP | 8-259882 A | 10/1996 |
| JP | 10-106822 A | 4/1998 |
| JP | 11-60720 A | 3/1999 |
| JP | 11-71440 A | 3/1999 |
| JP | 2866622 B2 | 3/1999 |
| JP | 11-131083 A | 5/1999 |
| JP | 2000-264883 A | 9/2000 |
| JP | 2001-134924 A | 5/2001 |
| JP | 2001-209924 A | 8/2001 |
| JP | 2002-69037 A | 3/2002 |
| JP | 2003113389 A | 4/2003 |
| JP | 2004-115640 A | 4/2004 |
| JP | 2004-346318 A | 12/2004 |
| JP | 2006-131874 A | 5/2006 |
| JP | 2009-266360 A | 11/2009 |
| JP | 2010-143855 A | 7/2010 |
| JP | 2010-241831 A | 10/2010 |
| JP | 2010-282707 A | 12/2010 |
| JP | 4632144 B2 | 2/2011 |
| JP | 2012-9090 A | 1/2012 |
| JP | 2012-33253 A | 2/2012 |
| JP | 2013-163667 A | 8/2013 |
| JP | 2013-181014 A | 9/2013 |
| JP | 2013-181140 A | 9/2013 |
| JP | 2014-509677 A | 4/2014 |
| JP | 5465454 B2 | 4/2014 |
| JP | 5613916 B2 | 10/2014 |
| JP | 5909837 B2 | 4/2016 |
| JP | 6122191 B1 | 4/2017 |
| JP | 2018-2673 A | 1/2018 |
| JP | 2018-24614 A | 2/2018 |
| JP | 2018-35348 A | 3/2018 |
| JP | 2018-076404 A | 5/2018 |
| JP | 2018-521183 A | 8/2018 |
| JP | 2018-178079 A | 11/2018 |
| WO | 98/17617 A1 | 4/1998 |
| WO | 2006/011387 A1 | 2/2006 |

(56) References Cited

FOREIGN PATENT DOCUMENTS

| WO | 2009/035075 A1 | 3/2009 |
| WO | 2009/123043 A1 | 10/2009 |
| WO | 2011/099131 A1 | 8/2011 |
| WO | 2012/170009 A2 | 12/2012 |
| WO | 2015/087615 A1 | 6/2015 |
| WO | 2015/199037 A1 | 12/2015 |
| WO | 2016/084781 A1 | 6/2016 |
| WO | 2017/005834 A1 | 1/2017 |
| WO | 2017/145995 A1 | 8/2017 |
| WO | 2017/154403 A1 | 9/2017 |
| WO | 2018/116742 A1 | 6/2018 |
| WO | 2018/139058 A1 | 8/2018 |
| WO | 2018/139174 A1 | 8/2018 |
| WO | 2018/147017 A1 | 8/2018 |
| WO | 2018/159232 A1 | 9/2018 |
| WO | 2019/039200 A | 2/2019 |
| WO | 2019/039265 A1 | 2/2019 |
| WO | 2019/049585 A1 | 3/2019 |
| WO | 2019/054148 A1 | 3/2019 |
| WO | 2019/087548 A1 | 5/2019 |

OTHER PUBLICATIONS

International Search Report for PCT/JP2020/047987, dated Feb. 16, 2021.
International Search Report for PCT/JP2020/033971 dated Nov. 24, 2020.
International Search Report for PCT/JP2020/041613, dated Dec. 28, 2020.
Office Action dated May 24, 2023 in U.S. Appl. No. 17/772,043.
"Cihai Sciences Volume 1" Edited by Cihai Editorial Committee, Shanghai Lexicographical Publishing House, Aug. 30, 1980, p. 329 (3 pages total).
Advisory Action dated Aug. 11, 2021, issued in U.S. Appl. No. 16/480,464.
Communication dated Dec. 24, 2019, from the Japanese Patent Office in Application No. 2016- 133653.
International Search Report for PCT/JP2017/003165 dated May 9, 2017.
International Search Report for PCT/JP2017/043451 dated Feb. 27, 2018.
International Search Report for PCT/JP2018/000071 dated Mar. 6, 2018.
International Search Report for PCT/JP2018/031161, dated Nov. 27, 2018.
International Search Report for PCT/JP2019/033697 dated Nov. 5, 2019.
International Search Report for PCT/JP2019/033700 dated Nov. 12, 2019.
International Search Report for PCT/JP2021/003708 dated Mar. 23, 2021.
Notice of Allowance dated Sep. 10, 2021 issued in U.S. Appl. No. 16/480,464.
Notice of Allowance dated Feb. 8, 2021 from the US Patent & Trademark Office in U.S. Appl. No. 15/640,729.
Notice of Allowance dated Nov. 16, 2021 from the US & Patent & Trademark Office in U.S. Appl. No. 16/082,349.
Notice of Allowance dated Feb. 9, 2023 in U.S. Appl. No. 17/274,702.
Notice of Allowance dated May 5, 2022 in U.S. Appl. No. 16/480,483.
Notice of Allowance dated Nov. 9, 2021 in U.S. Appl. No. 16/644,586.
Office Action dated Dec. 2, 2020 from the China National Intellectual Property Administration in CN Application No. 201780012469.9.
Office Action dated Jun. 8, 2021 from the US & Patent & Trademark Office in U.S. Appl. No. 16/082,349.
Office Action dated Mar. 11, 2021 from the China National Intellectual Property Administration in CN Application No. 201780070908.1.
Office Action dated May 13, 2020 from the US & Patent & Trademark Office in U.S. Appl. No. 15/640,729.
Office Action dated May 25, 2021 from the China National Intellectual Property Administration in CN Application No. 201780012469.9.
Office Action dated Nov. 12, 2020 from the US & Patent & Trademark Office in U.S. Appl. No. 15/640,729.
Office Action dated Oct. 29, 2019 from the US & Patent & Trademark Office in U.S. Appl. No. 15/640,729.
Final Office Action dated Apr. 16, 2021 Issued in U.S. Appl. No. 16/480,464.
Office Action dated Dec. 21, 2022 in U.S. Appl. No. 17/274,466.
Office Action dated Jan. 19, 2022 in U.S. Appl. No. 16/480,483.
Office Action dated Jan. 19, 2023 in U.S. Appl. No. 17/437,251.
Office Action dated Jul. 23, 2021 in U.S. Appl. No. 16/644,586.
Office Action dated Jun. 21, 2021 in U.S. Appl. No. 16/480,483.
Office Action dated Oct. 25, 2022 in U.S. Appl. No. 17/274,702.
Non-Final Office Action dated Jan. 28, 2021, issued in U.S. Appl. No. 16/480,464.
Restriction Election Requirement dated Nov. 23, 2020, issued in U.S. Appl. No. 16/480,464.
Office Action dated Jun. 7, 2023 in U.S. Appl. No. 17/797,177.
Supplemental Notice of Allowance dated Dec. 2, 2021 in U.S. Appl. No. 16/644,586.
Office Action dated Mar. 4, 2021 from the US & Patent & Trademark Office in U.S. Appl. No. 15/640,729.
International Search Report of PCT/JP2018/028455 dated Oct. 2, 2018.
Office Action dated May 7, 2022 issued by the Chinese Patent Office in Chinese Application No. 201880053594.9.
Office Action dated Sep. 15, 2022 in U.S. Appl. No. 16/640,132.
Notice of Allowance dated Jan. 5, 2023 in U.S. Appl. No. 16/640,132.
Office Action dated Jun. 10, 2019 in U.S. Appl. No. 15/640,729.
International Search Report of PCT/JP2020/010759 dated May 26, 2020.
Paul H. Kasai and Vedantham Raman, Perfluoropolyethers with dialklamine end groups: ultrastable lubricant for magnetic disk application.

* cited by examiner

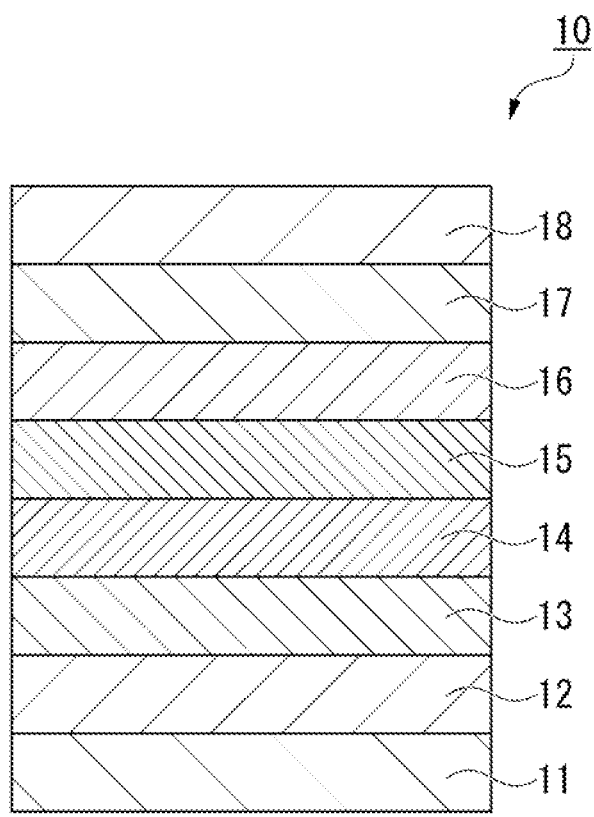

FLUORINE-CONTAINING ETHER COMPOUND, LUBRICANT FOR MAGNETIC RECORDING MEDIUM, AND MAGNETIC RECORDING MEDIUM

CROSS REFERENCE TO RELATED APPLICATIONS

This application is a National Stage of International Application No. PCT/JP2020/047987 filed Dec. 22, 2020, claiming priority based on Japanese Patent Application No. 2019-236885 filed Dec. 26, 2019, the content of which is incorporated herein by reference.

TECHNICAL FIELD

The present invention relates to a fluorine-containing ether compound, a lubricant for a magnetic recording medium and a magnetic recording medium.

BACKGROUND ART

The development of magnetic recording media suitable for high recording densities has progressed in order to improve the recording densities of magnetic recording/reproducing devices.

As a conventional magnetic recording medium, there has been a magnetic recording medium in which a recording layer is formed on a substrate and a protective layer made of carbon or the like is formed on the recording layer. The protective layer protects information recorded in the recording layer and enhances the slidability of a magnetic head. However, sufficient durability of the magnetic recording medium cannot be obtained by simply providing the protective layer on the recording layer. Therefore, generally, a lubricant is applied to the surface of the protective layer to form a lubricating layer.

As a lubricant that is used for forming a lubricating layer in a magnetic recording medium, for example, a lubricant containing a compound having a polar group such as a hydroxy group or an amino group at a terminal of a fluorine-based polymer having a repeating structure containing $CF_2$ has been proposed.

For example, Patent Document 1 discloses a fluoropolyether compound having an amino alcohol group at both molecule terminals. Patent Document 2 discloses a polymer which contains two perfluoropolyether chains linked by a divalent chain containing at least one hydroxy group and at least two amino groups, and having a monovalent chain containing a hydroxy group and an amino group at the terminal.

In addition, Patent Document 3 discloses a fluorine-containing ether compound in which a linking group that combines an ether bond (—O—), a methylene group (—CH$_2$—), and a methylene group in which one hydrogen atom is replaced with a hydroxy group (—CH(OH)—) is disposed between a perfluoropolyether chain and both terminal groups.

CITATION LIST

Patent Document

[Patent Document 1]
Japanese Unexamined Patent Application, First Publication No. H11-131083

[Patent Document 2]
Published Japanese Translation No. 2018-521183 of the PCT International Publication
[Patent Document 3]
PCT International Publication No. WO2019/054148

SUMMARY OF INVENTION

Technical Problem

There is a demand for a further decrease in a floating height of a magnetic head in magnetic recording/reproducing devices. This requires a further decrease in the thickness of a lubricating layer in magnetic recording media.

However, generally, if the thickness of the lubricating layer is reduced, the wear resistance of the magnetic recording medium tends to be lowered.

The present invention has been made in view of the above circumstances, and an object of the present invention is to provide a fluorine-containing ether compound which can form a lubricating layer having excellent wear resistance even if the thickness is thin, and can be suitably used as a material for a lubricant for a magnetic recording medium.

In addition, another object of the present invention is to provide a lubricant for a magnetic recording medium which contains the fluorine-containing ether compound of the present invention.

In addition, still another object of the present invention is to provide a magnetic recording medium having a lubricating layer containing the fluorine-containing ether compound of the present invention, and having excellent reliability and durability.

Solution to Problem

In order to achieve the above objects, the inventors conducted extensive studies.

As a result, it was found that a fluorine-containing ether compound in which a linking group having a specific structure in which —CH$_2$—, —O—, —NH—, and —CH(OH)— are combined and bonded in a chain is disposed between one or both terminal groups and a perfluoropolyether chain is preferable, and the present invention was completed.

That is, the present invention relates to the following matters. The present invention includes the following first aspect.

[1] A fluorine-containing ether compound represented by the following Formula (1):

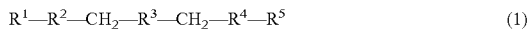

(in Formula (1), $R^3$ represents a perfluoropolyether chain; $R^1$ represents a terminal group bonded to $R^2$; $R^5$ represents a terminal group bonded to $R^4$; $R^1$ and $R^5$ each independently represent any of an alkyl group which may have a substituent, an organic group having a double bond or a triple bond, and a hydrogen atom; —$R^2$—CH$_2$—$R^3$ is represented by the following Formula (2); and $R^3$—CH$_2$—$R^4$— is represented by the following Formula (3)):

(in Formula (2), [A] is represented by the following Formula (4), [B] is represented by the following Formula (5); and in Formula (2), [A] and [B] may be interchanged), and (in Formula (3), [C] is represented by the following Formula (6), [D] is represented by the following Formula (7); and in Formula (3), [C] and [D] may be interchanged).

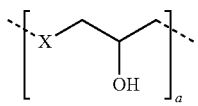

(4)

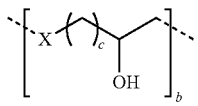

(5)

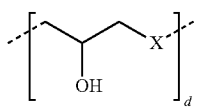

(6)

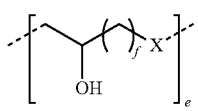

(7)

(a in Formula (4) and b in Formula (5) represent an integer of 0 to 2; c in Formula (5) represents an integer of 2 to 5; d in Formula (6) and e in Formula (7) represent an integer of 0 to 2; f in Formula (7) represents an integer of 2 to 5; at least one of b in Formula (5) and d in Formula (6) represents 1 or more; X represents any of O, NH, and $CH_2$; one or more of X's in Formulae (4) to (7) represent NH; and when X bonded to $R^1$ or $R^5$ represents NH, $R^1$ or $R^5$ represents either an alkyl group which may have a substituent or an organic group having a double bond or a triple bond).

The compound of the first aspect of the present invention preferably has the following features [2] to [12]. It is preferable to combine two or more of these features.

[2] The fluorine-containing ether compound according to [1],
wherein the number of secondary amine structures contained in the molecule is 2 or more.

[3] The fluorine-containing ether compound according to [1] or [2],
wherein the number of hydroxy groups contained in the molecule is 4 or less.

[4] The fluorine-containing ether compound according to any one of [1] to [3],
wherein a total number of secondary amine structures and hydroxy groups contained in the molecule is 7 or less.

[5] The fluorine-containing ether compound according to any one of [1] to [4],
wherein, in the molecule thereof, the number of secondary amine structures is 2 or more, the number of hydroxy groups is 4 or less, and a total number of secondary amine structures and hydroxy groups is 7 or less.

[6] The fluorine-containing ether compound according to any one of [1] to [5],
wherein, in Formula (1), $R^2$ represents any of the following Formulae (11-1) to (11-5):

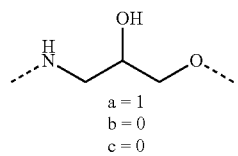

(11-1)

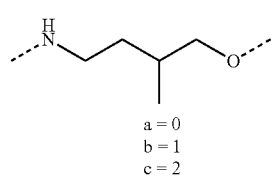

(11-2)

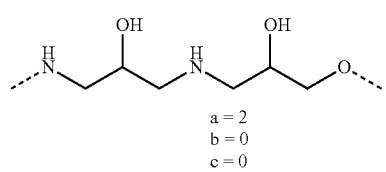

(11-3)

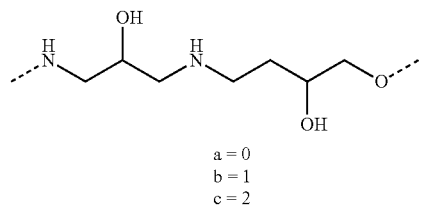

(11-4)

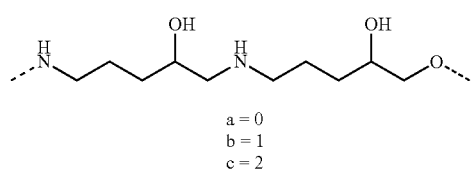

(11-5)

[7] The fluorine-containing ether compound according to any one of [1] to [6],
wherein the alkyl group which may have a substituent is an alkyl group having a hydroxy group and having 1 to 6 carbon atoms.

[8] The fluorine-containing ether compound according to any one of [1] to [7],
wherein the organic group having a double bond or a triple bond is any one of an aromatic hydrocarbon-containing group, an aromatic heterocycle-containing group, an alkenyl group, and an alkynyl group.

[9] The fluorine-containing ether compound according to any one of [1] to [8],
wherein, in Formula (1), $R^3$ represents any of the following Formulae (8) to (10):

$$—CF_2—(CF_2CF_2O)_m—(CF_2O)_n—CF_2—$$ (8)

(in Formula (8), m and n indicate an average degree of polymerization, and each represents 0 to 30; where, m or n is 0.1 or more), $$—CF(CF_3)—(OCF(CF_3)CF_2)_y—OCF(CF_3)—$$ (9)

(in Formula (9), y indicates an average degree of polymerization, and represents 0.1 to 30), and —$CF_2CF_2O$—$(CF_2CF_2CF_2O)_z$—$CF_2CF_2$— (10)

(in Formula (10), z indicates an average degree of polymerization, and represents 0.1 to 30).

[10] The fluorine-containing ether compound according to any one of [1] to [9], wherein a sum of a in Formula (4) and b in Formula (5), and a sum of d in Formula (6) and e in Formula (7) are each 1 or more.

[11] The fluorine-containing ether compound according to [1],
wherein the compound represented by Formula (1) is any of compounds represented by the following Formulae (K) to (M), (S), and (T):

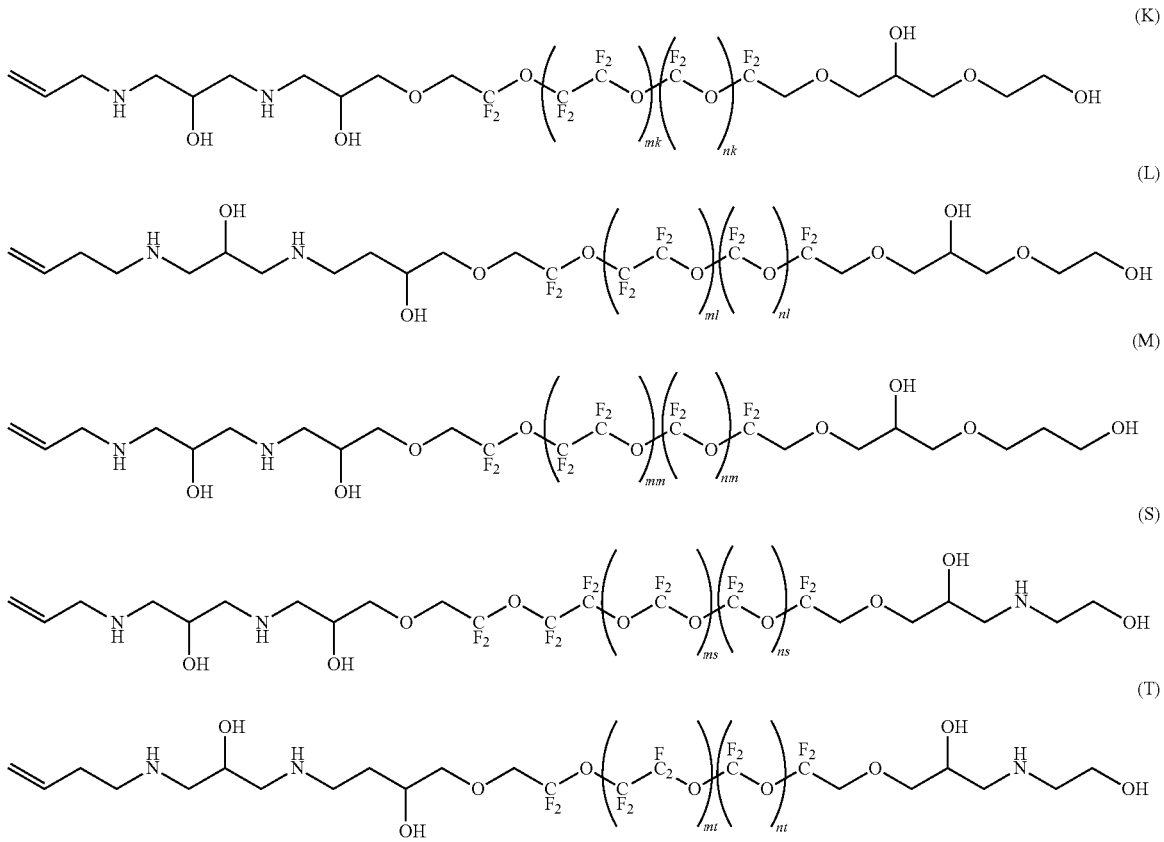

(in Formula (K), mk and nk indicate an average degree of polymerization, mk represents 1 to 30, and nk represents 0 to 30), (in Formula (L), ml and nl indicate an average degree of polymerization, ml represents 1 to 30, and nl represents 0 to 30), (in Formula (M), mm and nm indicate an average degree of polymerization, mm represents 1 to 30, and nm represents 0 to 30), (in Formula (S), ms and ns indicate an average degree of polymerization, ms represents 1 to 30, and ns represents 0 to 30), and (in Formula (T), mt and nt indicate an average degree of polymerization, mt represents 1 to 30, and nt represents 0 to 30).

[12] The fluorine-containing ether compound according to any one of [1] to [11],
wherein the number-average molecular weight thereof is in a range of 500 to 10,000.

A second aspect of the present invention is the following lubricant.

[13] A lubricant for a magnetic recording medium, which contains the fluorine-containing ether compound according to any one of [1] to [12].

A third aspect of the present invention is the following magnetic recording medium.

[14] A magnetic recording medium having at least a magnetic layer, a protective layer, and a lubricating layer sequentially provided on a substrate,
  wherein the lubricating layer contains the fluorine-containing ether compound according to any one of [1] to [12].

The magnetic recording medium preferably has the following feature.

[15] The magnetic recording medium according to [14], wherein the average film thickness of the lubricating layer is 0.5 nm to 2.0 nm.

Advantageous Effects of Invention

The fluorine-containing ether compound of the present invention is a compound represented by Formula (1), and is preferable as a material for a lubricant for a magnetic recording medium.

Since the lubricant for a magnetic recording medium of the present invention contains the fluorine-containing ether compound of the present invention, it is possible to form a lubricating layer having excellent wear resistance even if the thickness is thin.

Since the magnetic recording medium of the present invention has a lubricating layer having excellent wear resistance, it has excellent reliability and durability.

BRIEF DESCRIPTION OF DRAWINGS

The FIGURE is a schematic cross-sectional view showing an example of a preferable embodiment of a magnetic recording medium of the present invention.

DESCRIPTION OF EMBODIMENTS

Hereinafter, preferable examples of a fluorine-containing ether compound, a lubricant for a magnetic recording medium (hereinafter abbreviated as a "lubricant" in some cases) and a magnetic recording medium of the present invention will be described in detail. Here, the present invention is not limited only to the following embodiments. For example, the present invention is not limited only to the following examples, and numbers, amounts, ratios, compositions, types, positions, materials, configurations and the like can be added, omitted, substituted or changed without departing from the scope of the present invention.

[Fluorine-Containing Ether Compound]

A fluorine-containing ether compound of the present embodiment is represented by the following Formula (1):

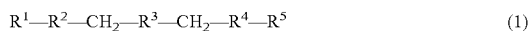

(in Formula (1), $R^3$ represents a perfluoropolyether chain; $R^1$ represents a terminal group bonded to $R^2$; $R^5$ represents a terminal group bonded to $R^4$; $R^1$ and $R^5$ each independently represent any of an alkyl group which may have a substituent, an organic group having a double bond or a triple bond, and a hydrogen atom; $-R^2-CH_2-R^3$ is represented by the following Formula (2); and $R^3-CH_2-R^4-$ is represented by the following Formula (3)):

(in Formula (2), [A] is represented by the following Formula (4), [B] is represented by the following Formula (5); and in Formula (2), [A] and [B] may be interchanged), and (in Formula (3), [C] is represented by the following Formula (6), [D] is represented by the following Formula (7); and in Formula (3), [C] and [D] may be interchanged).

(a in Formula (4) and b in Formula (5) represent an integer of 0 to 2; c in Formula (5) represents an integer of 2 to 5; d in Formula (6) and e in Formula (7) represent an integer of 0 to 2; f in Formula (7) represents an integer of 2 to 5; at least one of b in Formula (5) and d in Formula (6) represents 1 or more; X represents any of O, NH, and $CH_2$; one or more of X's in Formulae (4) to (7) represent NH; and when X bonded to $R^1$ or $R^5$ represents NH, $R^1$ or $R^5$ represents either an alkyl group which may have a substituent or an organic group having a double bond or a triple bond).

In the formulae, a, b, d and e may be any of 0, 1, and 2, and c and f may be any of 2, 3, 4, and 5.

Here, the reason why excellent wear resistance is obtained even if the thickness is thin when a lubricating layer is formed on the protective layer of the magnetic recording medium using the lubricant containing the fluorine-containing ether compound of the present embodiment will be described.

The fluorine-containing ether compound of the present embodiment has a perfluoropolyether chain (hereinafter abbreviated as "PFPE chain" in some cases) represented by $R^3$ as shown in Formula (1). In a lubricating layer containing the fluorine-containing ether compound of the present embodiment, the PFPE chain covers the surface of the protective layer, imparts lubricity to the lubricating layer, and reduces the frictional force between the magnetic head and the protective layer.

In addition, in Formula (1), $—R^2—CH_2—R^3$ is represented by Formula (2), and $R^3—CH_2—R^4—$ is represented by Formula (3). In Formula (2), [A] is represented by Formula (4), and [B] is represented by Formula (5). In addition, in Formula (3), [C] is represented by Formula (6), and [D] is represented by Formula (7). At least one of b in Formula (5) and d in Formula (6) is 1 or more, X in Formulae (4) to (7) is a divalent linking group bonded to the carbon atom in Formulae (4) to (7), and one or more of X's in Formulae (4) to (7) are NH.

Therefore, the fluorine-containing ether compound represented by Formula (1) contains a total of one or more hydroxy groups (—OH) and a total of one or more secondary amine structures (—NH—) in $R^2$ and $R^4$. In the lubricant containing the fluorine-containing ether compound of the present embodiment, the hydroxy group and the secondary amine structure contained in $R^2$ and $R^4$ cause the fluorine-containing ether compound and the protective layer to come into close contact with each other and improve wear resistance.

The hydroxy group (—OH) and the secondary amine structure (—NH—) of the fluorine-containing ether compound represented by Formula (1) have a polarity and have an interaction (affinity) with the protective layer and an intramolecular interaction. The interaction of the secondary amine structure with respect to the protective layer is the same as that of a hydroxy group. However, the intramolecular interaction of the secondary amine structure is weaker than that of a hydroxy group. Therefore, in —NH— contained in the fluorine-containing ether compound represented by Formula (1) on the protective layer, the interaction with the surface of the protective layer has priority over the intramolecular interaction. As a result, compared with a fluorine-containing ether compound having the same number of hydroxy groups as the number of —NH—'s in place of the —NH—'s contained in the fluorine-containing ether compound represented by Formula (1), the fluorine-containing ether compound represented by Formula (1) is less likely to aggregate on the protective layer and a thin lubricating layer can be formed with sufficient coverage. Accordingly, when the lubricant containing the fluorine-containing ether compound represented by Formula (1) is used, a lubricating layer having excellent wear resistance is obtained.

$R^2$ represents a divalent linking group, and $—R^2—CH_2—R^3$ is represented by Formula (2). In Formula (2), [A] is represented by Formula (4), and [B] is represented by Formula (5). In Formula (2), [A] and [B] may be interchanged. a in Formula (4) and b in Formula (5) represent an integer of 0 to 2, and c in Formula (5) represents an integer of 2 to 5.

In the lubricating layer containing the fluorine-containing ether compound, in order to further improve the adhesion between the fluorine-containing ether compound and the protective layer, at least one of a in Formula (4) and b in Formula (5) is preferably 1 or more (that is, Formula (2) includes at least one of [A] and [B]). The sum of a in Formula (4) and b in Formula (5) is 4 or less, and preferably 2 or less. When a sum of a in Formula (4) and b in Formula (5) is 2 or less, this is preferable because it is possible to prevent the occurrence of pickup in which the polarity of the fluorine-containing ether compound becomes too high and the compound adheres as foreign matter (smear) to a magnetic head.

c in Formula (5) represents an integer of 2 to 5, and is preferably an integer of 2 to 4 and most preferably 2. When c in Formula (5) is an integer of 2 to 5, it is preferable because the distance between the hydroxy group in Formula (5) and $R^1$ and/or the distance between hydroxy groups in Formula (5) becomes appropriate.

X in Formula (4) and Formula (5) is any of O, NH, and $CH_2$. When X bonded to $R^1$ is NH, $R^1$ is any of an alkyl group which may have a substituent and an organic group having a double bond or a triple bond, and is not a hydrogen atom.

$—R^2—$ in Formula (1) (-[A]-[B]—O— in Formula (2)) is preferably any of structures represented by the following Formulae (11-1) to (11-5), and Formulae (12-1) to (12-5). In the structures represented by Formulae (11-1) to (11-5) and Formulae (12-1) to (12-5), $R^1$ is bonded to the linking group (NH or O) disposed on the leftmost side.

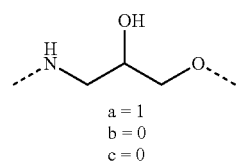

(11-1)

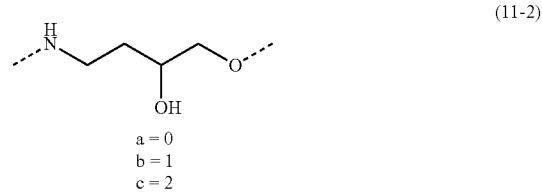

(11-2)

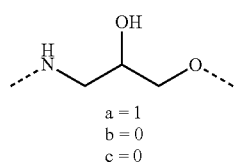
(11-1)
a = 1
b = 0
c = 0
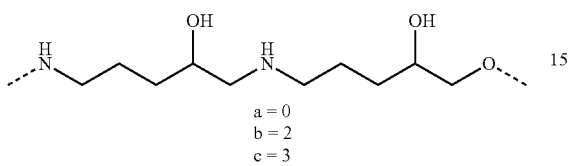
(11-5)
a = 0
b = 2
c = 3
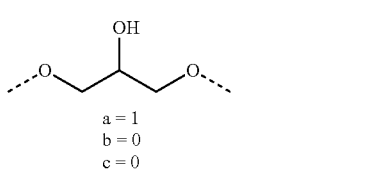
(12-1)
a = 1
b = 0
c = 0
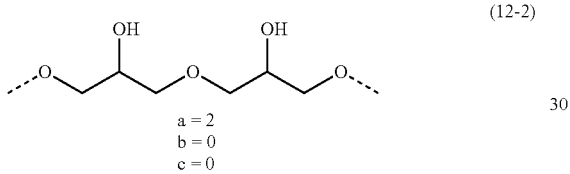
(12-2)
a = 2
b = 0
c = 0
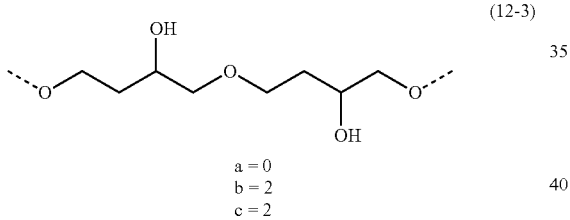
(12-3)
a = 0
b = 2
c = 2
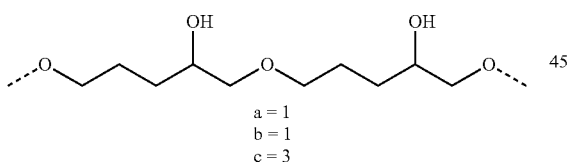
(12-4)
a = 1
b = 1
c = 3
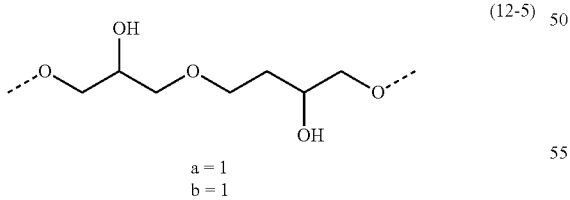
(12-5)
a = 1
b = 1
c = 2
In Formulae (11-1) to (11-5), and Formulae (12-1) to (12-5), a is a numerical value of a in Formula (4), and b and c are numerical values of b and c in Formula (5). Formulae (11-1) to (11-5) represent structures in which X in Formulae (4) and (5) is NH. Formulae (12-1) to (12-5) represent structures in which X in Formulae (4) and (5) is O.

In the fluorine-containing ether compound of the present embodiment, —$R^2$— in Formula (1) can be appropriately selected depending on the performance and the like required for the lubricant containing a fluorine-containing ether compound.

$R^4$ represents a divalent linking group, and $R^3$—$CH_2$—$R^4$— is represented by Formula (3). In Formula (3), [C] is represented by Formula (6), and [D] is represented by Formula (7). In Formula (3), [C] and [D] may be interchanged. d in Formula (6) and e in Formula (7) represent an integer of 0 to 2, and f in Formula (7) represents an integer of 2 to 5.

In the lubricating layer containing the fluorine-containing ether compound, in order to further improve the adhesion between the fluorine-containing ether compound and the protective layer, at least one of d in Formula (6) and e in Formula (7) is preferably 1 or more (that is, Formula (3) includes at least one of [C] and [D]). The sum of d in Formula (6) and e in Formula (7) is 4 or less, and preferably 2 or less. When the sum of d in Formula (6) and e in Formula (7) is 2 or less, this is preferable because it is possible to prevent the occurrence of pickup in which the polarity of the fluorine-containing ether compound becomes too high and the compound adheres as foreign matter (smear) to a magnetic head.

f in Formula (7) represents an integer of 2 to 5, and is preferably an integer of 2 to 4, and most preferably 2. When f in Formula (7) is an integer of 2 to 5, it is preferable because the distance between the hydroxy group in Formula (7) and $R^5$ and/or the distance between hydroxy groups in Formula (7) becomes appropriate.

X in Formula (6) and Formula (7) is any of O, NH, and $CH_2$. When X bonded to $R^5$ is NH, $R^5$ is any of an alkyl group which may have a substituent and an organic group having a double bond or a triple bond, and is not a hydrogen atom.

—$R^4$— in Formula (1) (—O—[C]-[D]- in Formula (3)) is preferably any of structures represented by the following Formulae (13-1) to (13-5), and Formulae (14-1) to (14-5). In the structures represented by Formulae (13-1) to (13-5) and Formulae (14-1) to (14-5), $R^5$ is bonded to the linking group (NH or O) disposed on the rightmost side.

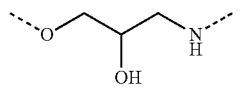

(13-1)

d = 1
e = 0
f = 0

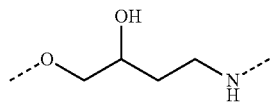

(13-2)

d = 0
e = 1
f = 2

-continued
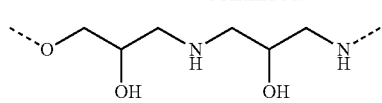
(13-3)
d = 2
e = 0
f = 0
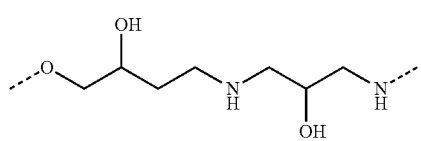
(13-4)
d = 1
e = 1
f = 2
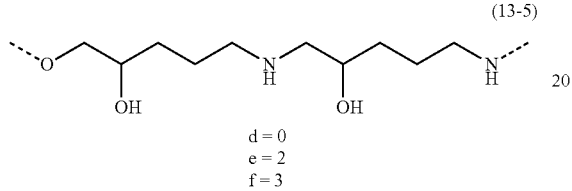
(13-5)
d = 0
e = 2
f = 3
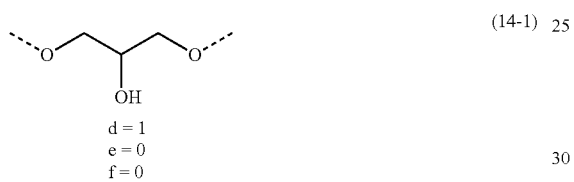
(14-1)
d = 1
e = 0
f = 0
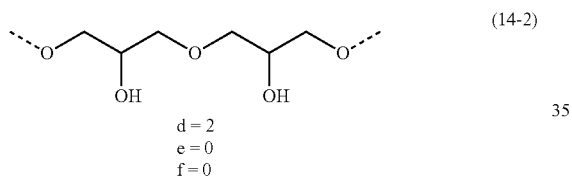
(14-2)
d = 2
e = 0
f = 0
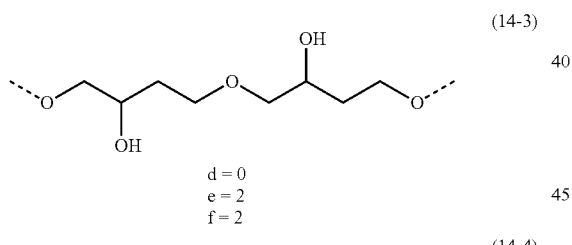
(14-3)
d = 0
e = 2
f = 2
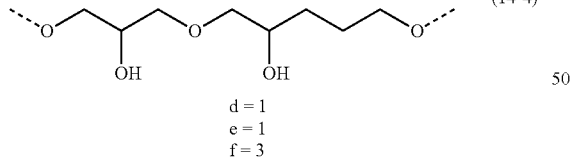
(14-4)
d = 1
e = 1
f = 3
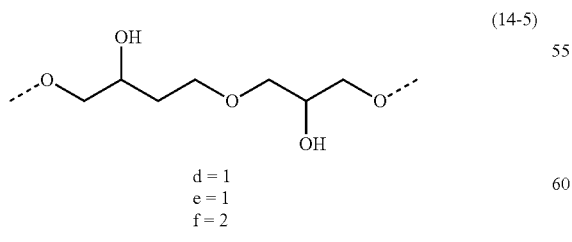
(14-5)
d = 1
e = 1
f = 2
In Formulae (13-1) to (13-5) and Formulae (14-1) to (14-5), d is a numerical value of d in Formula (6), and e and f are numerical values of e and f in Formula (7). Formulae (13-1) to (13-5) represent structures in which X in Formulae (6) and (7) is NH. Formulae (14-1) to (14-5) represent structures in which X in Formulae (6) and (7) is O.

In the fluorine-containing ether compound of the present embodiment, —$R^4$— in Formula (1) can be appropriately selected depending on the performance and the like required for the lubricant containing a fluorine-containing ether compound.

In the fluorine-containing ether compound of the present embodiment, at least one of b in Formula (5) and d in Formula (6) is 1 or more. Therefore, when both a in Formula (4) and e in Formula (7) are 0 (zero), and one of b in Formula (5) and d in Formula (6) is 0 (zero) (that is, not including [A] and [D] but including at least one of [B] and [C]), one of $R^2$ and $R^4$ in Formula (1) is an ether bond (—O—) in the fluorine-containing ether compound.

In the present embodiment, at least one of b in Formula (5) and d in Formula (6) is 1 or more, and it is preferable that a sum of a in Formula (4) and b in Formula (5) and a sum of d in Formula (6) and e in Formula (7) are each 1 or more.

In the fluorine-containing ether compound of the present embodiment, a sum of the number of hydroxy groups (—OH) contained in $R^2$ and the number of hydroxy groups contained in $R^4$ is 1 or more, and preferably 2 or more, and it is more preferable that $R^2$ and $R^4$ each contain 1 or more hydroxy groups. When $R^2$ and $R^4$ each contain 1 or more hydroxy groups, this is preferable because the adhesion between the fluorine-containing ether compound and the protective layer becomes better in the lubricating layer containing the fluorine-containing ether compound.

A sum of the number of hydroxy groups contained in $R^2$ and the number of hydroxy groups contained in $R^4$ is 8 or less, preferably 6 or less, and more preferably 4 or less. When a sum of the number of hydroxy groups contained in $R^2$ and the number of hydroxy groups contained in $R^4$ is 8 or less, this is preferable because it is possible to prevent the occurrence of pickup in which the polarity of the fluorine-containing ether compound becomes too high and the compound adheres as foreign matter (smear) to a magnetic head.

In the fluorine-containing ether compound represented by Formula (1), a total number of hydroxy groups contained in the molecule is preferably 6 or less, and more preferably 4 or less. When a total number of hydroxy groups contained in the molecule is 6 or less, the fluorine-containing ether compound is less likely to aggregate on the protective layer due to the intramolecular interaction of the hydroxy groups. Therefore, a thin lubricating layer can be formed with better coverage, and better wear resistance can be obtained.

In the fluorine-containing ether compound represented by Formula (1), in order to further improve the adhesion with the protective layer, a total number of secondary amine structures (—NH—) contained in the molecule is preferably 2 or more. In addition, when the total number of secondary amine structures (—NH—) contained in the molecule is 2 or more, it is more preferable that $R^2$ and $R^4$ each contain 1 or more secondary amine structures (—NH—). When $R^2$ and $R^4$ each contain 1 or more secondary amine structures (—NH—), the adhesion between the fluorine-containing ether compound and the protective layer becomes better in the lubricating layer containing the fluorine-containing ether compound.

In the fluorine-containing ether compound represented by Formula (1), a total number of hydroxy groups and secondary amine structures (—NH—) contained in the molecule is preferably 7 or less, and more preferably 6 or less. In this case, the fluorine-containing ether compound is less likely to aggregate on the protective layer due to the intramolecular interaction of the hydroxy groups, and a synergistic effect of the interaction with the protective layer due to the inclusion of the hydroxy group and the secondary amine structure is obtained. As a result, better wear resistance is obtained.

In the fluorine-containing ether compound represented by Formula (1) in the present embodiment, $R^1$ represents a terminal group bonded to $R^2$, and $R^5$ represents a terminal group bonded to $R^4$.

$R^1$ and $R^5$ each independently represent any of an alkyl group which may have a substituent, an organic group having a double bond or a triple bond, and a hydrogen atom. The alkyl group which may have a substituent and the organic group having a double bond or a triple bond may contain any of an oxygen atom, a sulfur atom, and a nitrogen atom.

In the alkyl group which may have a substituent, the alkyl group is preferably an alkyl group having 1 to 8 carbon atoms and more preferably an alkyl group having 1 to 6 carbon atoms. Specific examples thereof include a methyl group, ethyl group, propyl group, butyl group, pentyl group, hexyl group, heptyl group, and octyl group, which may be linear or have a branch.

In the alkyl group which may have a substituent, examples of substituents include a halogeno group, an alkoxy group, and a hydroxy group. When the alkyl group which may have a substituent has these substituents, a fluorine-containing ether compound which can form a lubricating layer having better wear resistance is obtained.

The alkyl group having a halogeno group as a substituent is preferably an alkyl group having at least one fluoro group. Examples of alkyl groups having a fluoro group include a trifluoromethyl group, perfluoroethyl group, perfluoropropyl group, perfluorobutyl group, perfluoropentyl group, perfluorohexyl group, octafluoropentyl group, and tridecafluorooctyl group.

The alkyl group having a hydroxy group as a substituent is preferably an alkyl group having a hydroxy group and having 1 to 6 carbon atoms, and more preferably an alkyl group represented by the following Formula (19-1). When at least one of $R^1$ and $R^5$ is an alkyl group represented by Formula (19-1), this is preferable because the affinity between the lubricating layer containing the fluorine-containing ether compound and the protective layer becomes better.

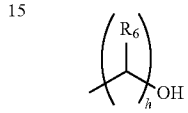

(19-1)

(in Formula (19-1), $R_6$ represents an alkyl group having 1 to 4 carbon atoms or a hydrogen atom, and h represents an integer of 1 to 6).

In Formula (19-1), $R_6$ represents an alkyl group having 1 to 4 carbon atoms or a hydrogen atom, and is preferably a hydrogen atom. In the structure represented by Formula (19-1), the left side is bonded to $R^2$ or $R^4$. In Formula (19-1), h represents an integer of 1 to 6, and is preferably an integer of 1 to 4, and more preferably 2 or 3. When the number of carbon atoms in Formula (19-1) (a total number of carbon atoms contained in $R_6$ and h) is 1 to 6, this is preferable because there is no decrease in the surface free energy of the entire molecule due to a low proportion of fluorine atoms in the fluorine-containing ether compound molecule.

The organic group having a double bond or a triple bond has at least one of a double bond and a triple bond, and examples thereof include an aromatic hydrocarbon-containing group, an aromatic heterocycle-containing group, an alkenyl group, and an alkynyl group. Specific examples of organic groups having a double bond or a triple bond include a phenyl group, methoxyphenyl group, phenylfluoride group, naphthyl group, phenethyl group, methoxyphenethyl group, phenethylfluoride group, benzyl group, methoxybenzyl group, naphthylmethyl group, methoxynaphthyl group, pyrrolyl group, pyrazolyl group, methylpyrazolylmethyl group, imidazolyl group, furyl group, furfuryl group, oxazolyl group, isooxazolyl group, thienyl group, thienylethyl group, thiazolyl group, methylthiazolylethyl group, isothiazolyl group, pyridyl group, pyrimidinyl group, pyridazinyl group, pyrazinyl group, indolinyl group, benzofuranyl group, benzothienyl group, benzoimidazolyl group, benzooxazolyl group, benzothiazolyl group, benzopyrazolyl group, benzoisooxazolyl group, benzoisothiazolyl group, quinolyl group, isoquinolyl group, quinazolinyl group, quinoxalinyl group, phthalazinyl group, cinnolinyl group, vinyl group, allyl group, butenyl group, propynyl group, propargyl group, butynyl group, methylbutynyl group, pentynyl group, methylpentynyl group, and hexynyl group.

Among the above examples, particularly, the organic group having a double bond or a triple bond is preferably any of a phenyl group, methoxyphenyl group, thienylethyl group, butenyl group, allyl group, propargyl group, phenethyl group, methoxyphenethyl group, and phenethylfluoride group, and more preferably a phenyl group, thienylethyl group, allyl group, or butenyl group. When the organic group having a double bond or a triple bond is any of a phenyl group, thienylethyl group, allyl group, and butenyl group, a fluorine-containing ether compound which can form a lubricating layer having better wear resistance is

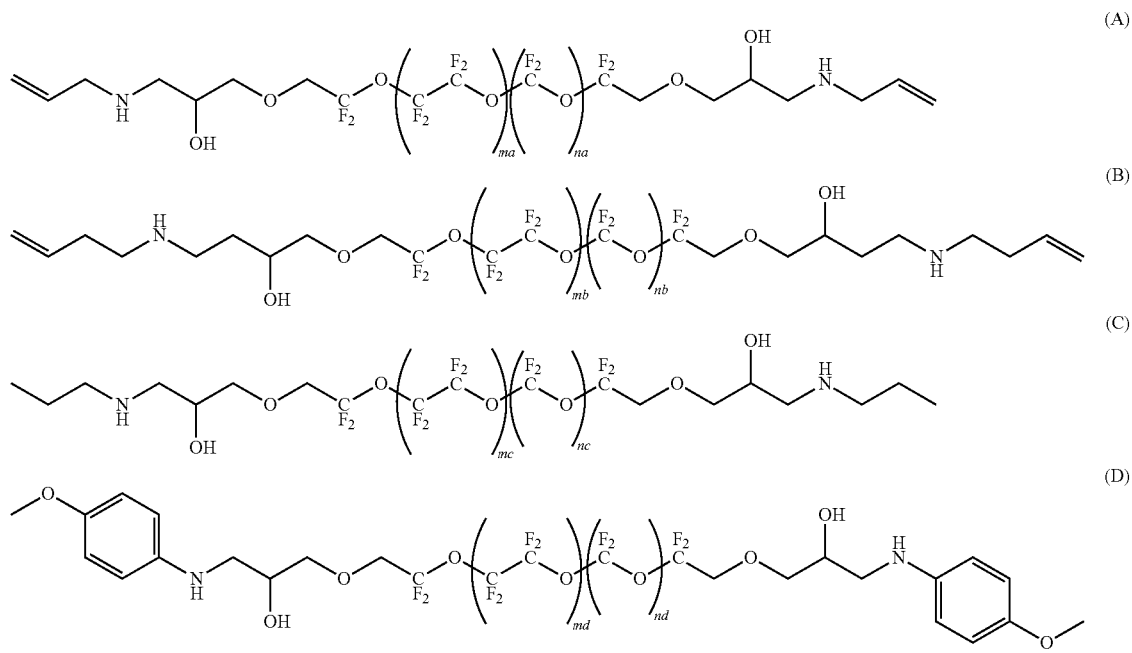

(in Formula (A), ma and na indicate the average degree of polymerization, ma represents 1 to 30, and na represents 0 to 30), (in Formula (B), mb and nb indicate the average degree of polymerization, mb represents 1 to 30, and nb represents 0 to 30), (in Formula (C), mc and nc indicate the average degree of polymerization, mc represents 1 to 30, and nc represents 0 to 30), and (in Formula (D), md and nd indicates the average degree of polymerization, md represents 1 to 30, and nd represents 0 to 30).

(in Formula (E), me and ne indicate the average degree of polymerization, me represents 1 to 30, and ne represents 0 to 30), (in Formula (F), mf and nf indicate the average degree of polymerization, mf represents 1 to 30, and nf represents 0 to 30), (in Formula (G), mg and ng indicate the average degree of polymerization, mg represents 1 to 30, and ng represents 0 to 30), and (in Formula (H), mh and nh indicate the average degree of polymerization, mh represents 1 to 30, and nh represents 0 to 30).

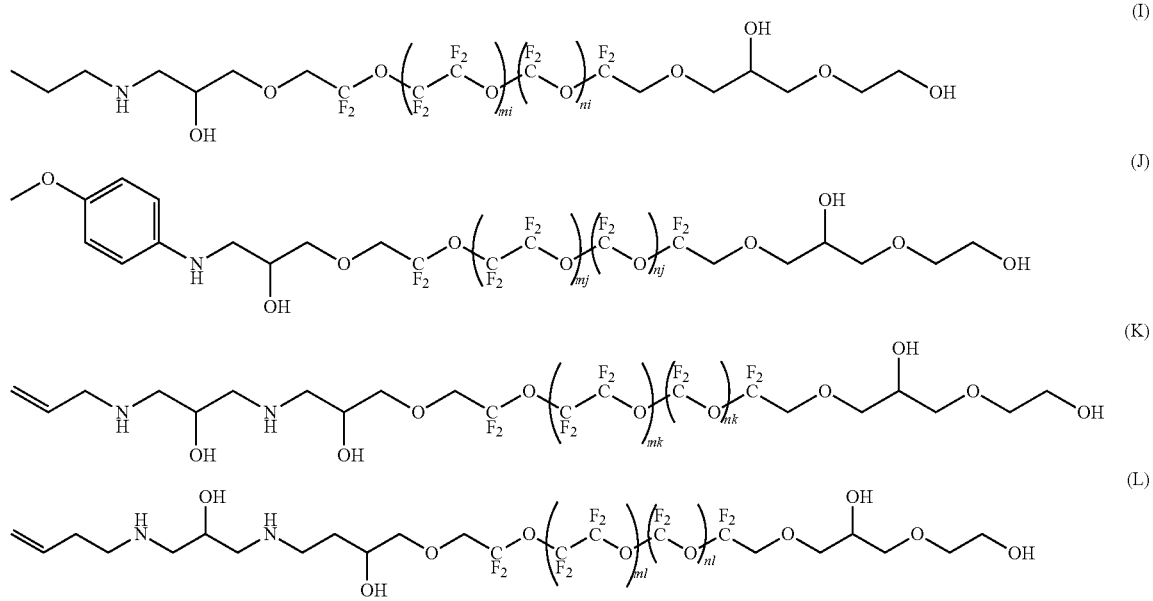

(in Formula (I), mi and ni indicate the average degree of polymerization, mi represents 1 to 30, and ni represents 0 to 30), (in Formula (J), mj and nj indicate the average degree of polymerization, mj represents 1 to 30, and nj represents 0 to 30), (in Formula (K), mk and nk indicate the average degree of polymerization, mk represents 1 to 30, and nk represents 0 to 30), and (in Formula (L), ml and nl indicate the average degree of polymerization, ml represents 1 to 30, and nl represents 0 to 30).

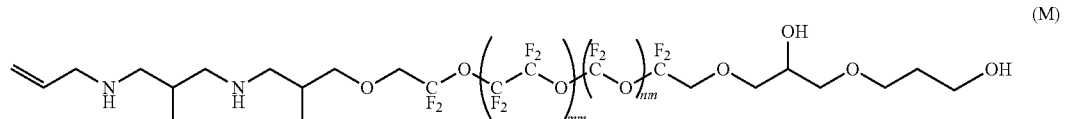

(in Formula (M), mm and nm indicate the average degree of polymerization, mm represents 1 to 30, and nm represents 0 to 30), (in Formula (N), nm and nn indicate the average degree of polymerization, nm represents 1 to 30, and nn represents 0 to 30), (in Formula (O), mo and no indicate the average degree of polymerization, mo represents 1 to 30, and no represents 0 to 30), and (in Formula (P), mp and np indicate the average degree of polymerization, mp represents 1 to 30, and np represents 0 to 30).

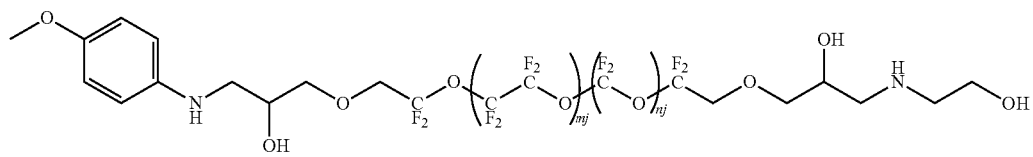
(Q)

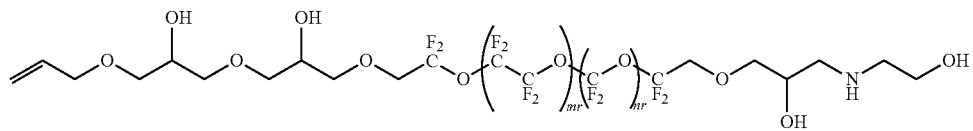
(R)

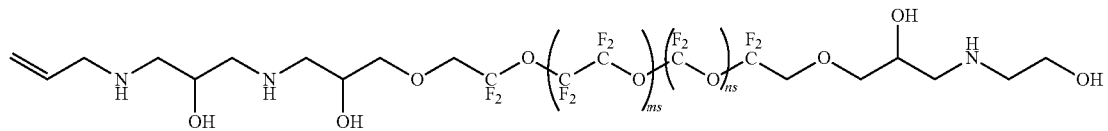
(S)

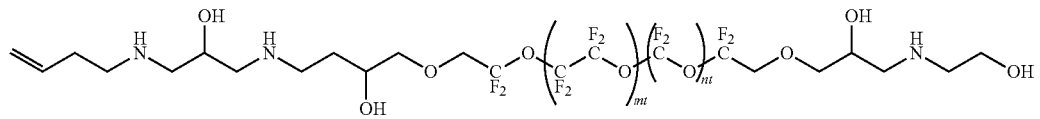
(T)

(in Formula (Q), mq and nq indicate the average degree of polymerization, mq represents 1 to 30, and nq represents 0 to 30), (in Formula (R), mr and nr indicate the average degree of polymerization, mr represents 1 to 30, and nr represents 0 to 30), (in Formula (S), ms and ns indicate the average degree of polymerization, ms represents 1 to 30, and ns represents 0 to 30), and (in Formula (T), mt and nt indicate the average degree of polymerization, mt represents 1 to 30, and nt represents 0 to 30).

(in Formula (U), mu and nu indicate the average degree of polymerization, mu represents 1 to 30, and nu represents 0 to 30),
(in Formula (V), my and nv indicate the average degree of polymerization, my represents 1 to 30, and nv represents 0 to 30), and
(in Formula (W), mw and nw indicate the average degree of polymerization, mw represents 1 to 30, and nw represents 0 to 30).
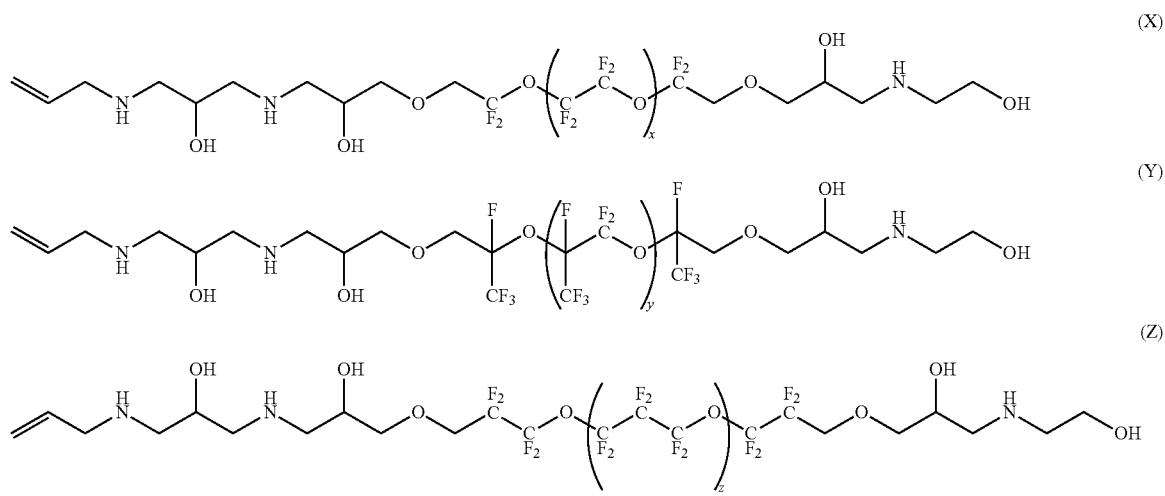

(in Formula (X), x indicates the average degree of polymerization, and x represents 0.1 to 30), (in Formula (Y), y indicates the average degree of polymerization, and y represents 0.1 to 30), and (in Formula (Z), z indicates the average degree of polymerization, and z represents 0.1 to 30).

When the compound represented by Formula (1) is any of the compounds represented by Formulae (A) to (Z), this is preferable because a raw material is easily available, and it is possible to form a lubricating layer having excellent wear resistance even if the thickness is thin.

The number-average molecular weight (Mn) of the fluorine-containing ether compound of the present embodiment is preferably in a range of 500 to 10,000. When the number-average molecular weight is 500 or more, the lubricant containing the fluorine-containing ether compound of the present embodiment is less likely to evaporate, and it is possible to prevent the lubricant from evaporating and transferring to a magnetic head. The number-average molecular weight of the fluorine-containing ether compound is more preferably 1,000 or more. In addition, when the number-average molecular weight is 10,000 or less, the viscosity of the fluorine-containing ether compound becomes appropriate, and a thin lubricating layer can be easily formed by applying the lubricant containing the compound. The number-average molecular weight of the fluorine-containing ether compound is more preferably 3,000 or less so that the compound has a viscosity at which handling is easy when applied to a lubricant.

The number-average molecular weight (Mn) of the fluorine-containing ether compound is a value measured through $^1$H-NMR and $^{19}$F-NMR of AVANCEIII400 (commercially available from Bruker BioSpin). In the measurement of nuclear magnetic resonance (NMR), a sample is diluted with a single solvent or a mixed solvent of hexafluorobenzene, d-acetone, d-tetrahydrofuran and the like, and used for measurement. The standard for $^{19}$F-NMR chemical shift is −164.7 ppm for the peak of hexafluorobenzene, and the standard for $^1$H-NMR chemical shift is 2.2 ppm for the peak of acetone.

"Production Method"

A method of producing a fluorine-containing ether compound of the present embodiment is not particularly limited, and a conventionally known production method can be used for production. The fluorine-containing ether compound of the present embodiment can be produced using, for example, the following production method.

First, a fluorine-based compound in which a hydroxymethyl group ($-CH_2OH$) is disposed at both terminals of the perfluoropolyether chain corresponding to $R^3$ in Formula (1) is prepared.

Next, the hydroxy group of the hydroxymethyl group disposed at one terminal of the fluorine-based compound is replaced with a group composed of $R^1-R^2-$ in Formula (1) (first reaction). Then, the hydroxy group of the hydroxymethyl group disposed at the other terminal is replaced with the terminal group composed of $-R^4-R^5$ in Formula (1) (second reaction).

The first reaction and the second reaction can be performed using a conventionally known method, and can be appropriately determined according to the types of $R^1$, $R^2$, $R^4$, and $R^5$ and the like in Formula (1). In addition, either the first reaction or the second reaction may be performed first. When $R^1$ and $R^5$ are the same, and $R^2$ and $R^4$ are the same, the first reaction and the second reaction may be performed at the same time.

According to the above method, a compound represented by Formula (1) is obtained.

In the present embodiment, in order to produce a fluorine-containing ether compound in which $-R^2-CH_2-R^3$ is represented by Formula (2), and $R^3-CH_2-R^4-$ is represented by Formula (3), it is preferable to use an epoxy compound. For the epoxy compound, a commercial product may be purchased or the compound may be synthesized. When the epoxy compound is synthesized, it can be synthesized using an alcohol or a protected amine having a structure corresponding to the terminal group represented by $R^1$ or $R^5$ of the fluorine-containing ether compound to be produced, and any one selected from among epichlorohydrin, epibromohydrin, and 2-bromoethyloxirane. In addition, the epoxy compound may be synthesized by a method of oxidizing an unsaturated bond.

The fluorine-containing ether compound of the present embodiment is a compound represented by Formula (1). Therefore, when a lubricating layer is formed on the protective layer using the lubricant containing the compound, the PFPE chain represented by $R^3$ in Formula (1) covers the surface of the protective layer and reduces the frictional force between the magnetic head and the protective layer.

In addition, in the lubricating layer formed using the lubricant containing the fluorine-containing ether compound of the present embodiment, excellent wear resistance is obtained by the intramolecular interaction between terminal groups represented by $R^1$ and $R^5$ and a total of one or more hydroxy groups and a total of one or more secondary amine structures ($-NH-$) contained in $R^2$ and $R^4$.

In addition, in the fluorine-containing ether compound of the present embodiment, the PFPE chain is adhered onto the protective layer by the interaction between the terminal groups represented by $R^1$ and $R^5$, a total of one or more hydroxy groups and a total of one or more secondary amine structures contained in $R^2$ and $R^4$ linked to the PFPE chain, and the protective layer. Therefore, according to the fluorine-containing ether compound of the present embodiment, the lubricating layer and the protective layer are firmly bonded, and a lubricating layer having excellent wear resistance is obtained.

[Lubricant for Magnetic Recording Medium]

A lubricant for a magnetic recording medium of the present embodiment contains a fluorine-containing ether compound represented by Formula (1).

The lubricant of the present embodiment can be used by being mixed with a known material used as a material for a lubricant as necessary as long as the characteristics of the fluorine-containing ether compound represented by Formula (1) are not impaired due to the inclusion of the material.

Specific examples of known materials include, for example, FOMBLIN (registered trademark) ZDIAC, FOMBLIN ZDEAL, and FOMBLIN AM-2001 (all commercially available from Solvay Solexis), and Moresco A20H (commercially available from Moresco). A known material used in combination with the lubricant of the present embodiment preferably has a number-average molecular weight of 1,000 to 10,000.

When the lubricant of the present embodiment contains a material other than the fluorine-containing ether compound represented by Formula (1), the content of the fluorine-containing ether compound represented by Formula (1) in the lubricant of the present embodiment is preferably 50 mass % or more, and more preferably 70 mass % or more. The upper limit can be arbitrarily selected, and for example, it may be 99 mass % or less, 95 mass % or less, 90 mass % or less, or 85 mass % or less.

Since the lubricant of the present embodiment contains the fluorine-containing ether compound represented by Formula (1), it can cover the surface of the protective layer with high coverage even if the thickness is thin, and form a lubricating layer having excellent adhesion to the protective layer. Therefore, according to the lubricant of the present embodiment, a lubricating layer having excellent wear resistance even if the thickness is thin is obtained.

In addition, since the lubricant of the present embodiment contains the fluorine-containing ether compound represented by Formula (1), the fluorine-containing ether compound in the lubricant layer that is present without adhering (adsorbing) to the protective layer is less likely to aggregate. Therefore, it is possible to prevent the fluorine-containing ether compound from aggregating and adhering as foreign matter (smear) to a magnetic head, and reduce the occurrence of pickup.

In addition, since the lubricant of the present embodiment contains the fluorine-containing ether compound represented by Formula (1), it is possible to form a lubricating layer having excellent wear resistance by the interaction between the terminal groups represented by $R^1$ and $R^5$ in Formula (1), a total of one or more hydroxy groups (—OH) and a total of one or more secondary amine structures (—NH—) contained in $R^2$ and $R^4$, and the protective layer.

[Magnetic Recording Medium]

In a magnetic recording medium of the present embodiment, at least a magnetic layer, a protective layer, and a lubricating layer are sequentially provided on a substrate.

In the magnetic recording medium of the present embodiment, as necessary, one, two or more underlayers can be provided between the substrate and the magnetic layer. In addition, an adhesive layer and/or a soft magnetic layer can be provided between the underlayer and the substrate.

The FIGURE is a schematic cross-sectional view showing a magnetic recording medium according to one embodiment of the present invention.

A magnetic recording medium 10 of the present embodiment has a structure in which an adhesive layer 12, a soft magnetic layer 13, a first underlayer 14, a second underlayer 15, a magnetic layer 16, a protective layer 17, and a lubricating layer 18 are sequentially provided on a substrate 11.

"Substrate"

The substrate 11 can be arbitrarily selected. As the substance 11, for example, a non-magnetic substrate in which a film made of NiP or a NiP alloy is formed on a base made of a metal or an alloy material such as Al or an Al alloy can be preferably used.

In addition, as the substrate 11, a non-magnetic substrate made of a non-metal material such as glass, a ceramic, silicon, silicon carbide, carbon, and a resin may be used, or a non-magnetic substrate in which a film of NiP or a NiP alloy is additionally formed on a base made of these non-metal materials may be used as the substrate 11.

"Adhesive Layer"

The adhesive layer 12 prevents the progress of corrosion of the substrate 11 that occurs when the substrate 11 and the soft magnetic layer 13 provided on the adhesive layer 12 are disposed in contact with each other.

The material of the adhesive layer 12 can be arbitrarily selected, and can be appropriately selected from among, for example, Cr, a Cr alloy, Ti, a Ti alloy, CrTi, NiAl, and an AlRu alloy. The adhesive layer 12 can be formed by, for example, a sputtering method.

"Soft Magnetic Layer"

The soft magnetic layer 13 can be arbitrarily selected and preferably has a structure in which a first soft magnetic film, an intermediate layer made of a Ru film and a second soft magnetic film are sequentially laminated. That is, the soft magnetic layer 13 preferably has a structure in which an intermediate layer made of a Ru film is interposed between two soft magnetic film layers, and thus the soft magnetic films above and below the intermediate layer are bonded by anti-ferromagnetic coupling (AFC).

Examples of materials of the first soft magnetic film and the second soft magnetic film include a CoZrTa alloy and a CoFe alloy.

It is preferable to add any of Zr, Ta, and Nb to the CoFe alloy used for the first soft magnetic film and the second soft magnetic film. Thereby, the amorphization of the first soft magnetic film and the second soft magnetic film can be promoted, the orientation of the first underlayer (seed layer) can be improved, and the floating height of the magnetic head can be reduced.

The soft magnetic layer 13 can be formed by, for example, a sputtering method.

"First Underlayer"

The first underlayer 14 is a layer that controls the orientation and the crystal size of the second underlayer 15 and the magnetic layer 16 provided thereon.

Examples of the first underlayer 14 include a Cr layer, a Ta layer, a Ru layer, and CrMo, CoW, CrW, CrV, and CrTi alloy layers.

The first underlayer 14 can be formed by, for example, a sputtering method.

"Second Underlayer"

The second underlayer 15 is a layer that controls the orientation of the magnetic layer 16 such that it becomes favorable. The second underlayer 15 can be arbitrarily selected, but it is preferably a layer made of Ru or a Ru alloy. The second underlayer 15 may be a single layer or may be composed of a plurality of layers. When the second underlayer 15 is composed of a plurality of layers, all of the layers may be composed of the same material, or at least one layer may be composed of a different material.

The second underlayer 15 can be formed by, for example, a sputtering method.

"Magnetic Layer"

The magnetic layer 16 is made of a magnetic film in which the axis of easy magnetization is in a direction perpendicular or horizontal to the surface of the substrate. The magnetic layer 16 can be arbitrarily selected, and is preferably a layer containing Co and Pt, and may be a layer containing an oxide, Cr, B, Cu, Ta, Zr or the like in order to further improve SNR characteristics.

Examples of oxides contained in the magnetic layer 16 include $SiO_2$, SiO, $Cr_2O_3$, CoO, $Ta_2O_3$, and $TiO_2$.

The magnetic layer 16 may be composed of a single layer or may be composed of a plurality of magnetic layers made of materials with different compositions.

For example, when the magnetic layer 16 is composed of three layers including a first magnetic layer, a second magnetic layer, and a third magnetic layer sequentially laminated from below, the first magnetic layer preferably has a granular structure made of a material containing Co, Cr, and Pt, and further containing an oxide. As the oxide contained in the first magnetic layer, for example, it is preferable to use an oxide of Cr, Si, Ta, Al, Ti, Mg, Co or the like. Among these, particularly, $TiO_2$, $Cr_2O_3$, $SiO_2$ or the like can be preferably used. In addition, the first magnetic layer is preferably made of a composite oxide in which two or more oxides are added. Among these, particularly, $Cr_2O_3$—$SiO_2$, $Cr_2O_3$—$TiO_2$, $SiO_2$—$TiO_2$ or the like can be preferably used.

The first magnetic layer can contain one or more elements selected from among B, Ta, Mo, Cu, Nd, W, Nb, Sm, Tb, Ru, and Re in addition to Co, Cr, Pt, and an oxide.

For the second magnetic layer, the same material as for the first magnetic layer can be used. The second magnetic layer preferably has a granular structure.

The third magnetic layer preferably has a non-granular structure made of a material containing Co, Cr, and Pt, and not containing an oxide. The third magnetic layer can contain one or more elements selected from among B, Ta, Mo, Cu, Nd, W, Nb, Sm, Tb, Ru, Re, and Mn in addition to Co, Cr, and Pt.

When the magnetic layer 16 is formed of a plurality of magnetic layers, it is preferable to provide a non-magnetic layer between adjacent magnetic layers. When the magnetic layer 16 is composed of three layers including a first magnetic layer, a second magnetic layer, and a third magnetic layer, it is preferable to provide a non-magnetic layer between the first magnetic layer and the second magnetic layer, and between the second magnetic layer and the third magnetic layer.

For the non-magnetic layer provided between adjacent magnetic layers of the magnetic layer 16, for example, Ru, a Ru alloy, a CoCr alloy, a CoCrX1 alloy (X1 represents one, two or more elements selected from among Pt, Ta, Zr, Re, Ru, Cu, Nb, Ni, Mn, Ge, Si, O, N, W, Mo, Ti, V, and B), or the like can be preferably used.

For the non-magnetic layer provided between adjacent magnetic layers of the magnetic layer 16, it is preferable to use an alloy material containing an oxide, a metal nitride, or a metal carbide. Specifically, as the oxide, for example, $SiO_2$, $Al_2O_3$, $Ta_2O_5$, $Cr_2O_3$, MgO, $Y_2O_3$, $TiO_2$ or the like can be used. As the metal nitride, for example, AlN, $Si_3N_4$, TaN, CrN or the like can be used. As the metal carbide, for example, TaC, BC, SiC or the like can be used.

The non-magnetic layer can be formed by, for example, a sputtering method.

The magnetic layer 16 is preferably a magnetic layer for perpendicular magnetic recording in which the axis of easy magnetization is in a direction perpendicular to the surface of the substrate in order to realize a higher recording density. The magnetic layer 16 may be a magnetic layer for in-plane magnetic recording.

The magnetic layer 16 may be formed by any conventionally known method such as a deposition method, an ion beam sputtering method, and a magnetron sputtering method. The magnetic layer 16 is generally formed by a sputtering method.

"Protective Layer"

The protective layer 17 protects the magnetic layer 16. The protective layer 17 may be composed of one layer or may be composed of a plurality of layers. Examples of materials of the protective layer 17 include carbon, carbon containing nitrogen, and silicon carbide.

As the protective layer 17, a carbon-based protective layer can be preferably used, and an amorphous carbon protective layer is particularly preferable. When the protective layer 17 is a carbon-based protective layer, this is preferable because the interaction with the polar group (particularly the hydroxy group) contained in the fluorine-containing ether compound in the lubricating layer 18 is further improved.

The adhesive force between the carbon-based protective layer and the lubricating layer 18 can be controlled by forming the carbon-based protective layer with hydrogenated carbon and/or nitrogenated carbon and adjusting the hydrogen content and/or the nitrogen content in the carbon-based protective layer. The hydrogen content in the carbon-based protective layer measured by a hydrogen forward scattering method (HFS) is preferably 3 to 20 atomic %. In addition, the nitrogen content in the carbon-based protective layer measured through X-ray photoelectron spectroscopy (XPS) is preferably 4 to 15 atomic %.

Hydrogen and/or nitrogen contained in the carbon-based protective layer need not be uniformly contained throughout the entire carbon-based protective layer. For example, the carbon-based protective layer is preferably formed as a composition gradient layer in which nitrogen is contained in the protective layer 17 on the side of the lubricating layer 18 and hydrogen is contained in the protective layer 17 on the side of the magnetic layer 16. In this case, the adhesive force between the magnetic layer 16 and the lubricating layer 18, and the carbon-based protective layer is further improved.

The film thickness of the protective layer 17 may be 1 nm to 7 nm. When the film thickness of the protective layer 17 is 1 nm or more, the performance of the protective layer 17 can be sufficiently obtained. The film thickness of the protective layer 17 is preferably 7 nm or less in order to reduce the thickness of the protective layer 17.

As a film forming method for the protective layer 17, a sputtering method using a target material containing carbon, a chemical vapor deposition (CVD) method using a hydrocarbon raw material such as ethylene or toluene, an ion beam deposition (IBD) method or the like can be used.

When a carbon-based protective layer is formed as the protective layer 17, for example, a film can be formed by a DC magnetron sputtering method. In particular, when a carbon-based protective layer is formed as the protective layer 17, it is preferable to form an amorphous carbon protective layer by a plasma CVD method. The amorphous carbon protective layer formed by the plasma CVD method has a uniform surface and low roughness.

"Lubricating Layer"

The lubricating layer 18 prevents contamination of the magnetic recording medium 10. In addition, the lubricating layer 18 reduces a frictional force of a magnetic head of a magnetic recording/reproducing device, which slides on the magnetic recording medium 10, and improves the durability of the magnetic recording medium 10.

As shown in the FIGURE, the lubricating layer 18 is formed on and in contact with the protective layer 17. The lubricating layer 18 contains the above fluorine-containing ether compound.

When the protective layer 17 disposed below the lubricating layer 18 is a carbon-based protective layer, the lubricating layer 18 is bonded to the protective layer 17 with a particularly high bonding force. As a result, even if the thickness of the lubricating layer 18 is thin, it is easy to obtain the magnetic recording medium 10 in which the surface of the protective layer 17 is covered with high coverage, and it is possible to effectively prevent contamination of the surface of the magnetic recording medium 10.

The average film thickness of the lubricating layer 18 can be arbitrarily selected, and is preferably 0.5 nm (5 Å) to 2.0 nm (20 Å), and more preferably 0.5 nm (5 Å) to 1.0 nm (10 Å). When the average film thickness of the lubricating layer 18 is 0.5 nm or more, the lubricating layer 18 is formed with a uniform film thickness without forming an island shape or a mesh shape. Therefore, the lubricating layer 18 can cover the surface of the protective layer 17 with high coverage. In addition, when the average film thickness of the lubricating layer 18 is 2.0 nm or less, the lubricating layer 18 can be sufficiently thinned, and the floating height of the magnetic head can be sufficiently reduced.

When the surface of the protective layer 17 is not sufficiently covered with the lubricating layer 18 with high coverage, environmental substances adsorbed on the surface of the magnetic recording medium 10 pass through voids of the lubricating layer 18 and enter a layer below the lubricating layer 18. The environmental substances that have entered the layer below the lubricating layer 18 are adsorbed and bonded to the protective layer 17 and produce contamination substances. Thus, during magnetic recording/reproducing, the contamination substances (aggregated components) adhere (transfer) to a magnetic head as a smear, the magnetic head may be damaged, and magnetic recording/reproducing characteristics of the magnetic recording/reproducing device may deteriorate.

Examples of environmental substances that produce contamination substances include siloxane compounds (cyclic siloxane and linear siloxane), ionic impurities, hydrocarbons having a relatively high molecular weight such as octacosane, and plasticizers such as dioctyl phthalate. Examples of metal ions contained in ionic impurities include sodium ions and potassium ions. Examples of inorganic ions contained in ionic impurities include chloride ions, bromine ions, nitrate ions, sulfate ions, and ammonium ions. Examples of organic ions contained in ionic impurities include oxalate ions and formate ions.

"Method of Forming Lubricating Layer"

Examples of a method of forming the lubricating layer 18 include a method in which a magnetic recording medium during production in which respective layers up to the protective layer 17 are formed on the substrate 11 is prepared, and a solution for forming a lubricating layer is applied onto the protective layer 17 and dried.

The solution for forming a lubricating layer can be obtained by dispersing and dissolving the lubricant for a magnetic recording medium of the embodiment described above in a solvent as necessary, and adjusting the viscosity and concentration to be suitable for application methods.

Examples of solvents used for the solution for forming a lubricating layer include fluorine-based solvents such as Vertrel (registered trademark) XF (product name, commercially available from Du Pont-Mitsui Fluorochemicals Co., Ltd.).

The method of applying the solution for forming a lubricating layer is not particularly limited, and examples thereof include a spin coating method, a spraying method, a paper coating method, and a dipping method.

When the dipping method is used, for example, the following method can be used. First, the substrate 11 in which respective layers up to the protective layer 17 are formed is immersed in the solution for forming a lubricating layer contained in an immersion vessel of a dip coating device. Next, the substrate 11 is lifted from the immersion vessel at a predetermined speed. Accordingly, the solution for forming a lubricating layer is applied to the surface of the protective layer 17 of the substrate 11.

When the dipping method is used, the solution for forming a lubricating layer can be uniformly applied to the surface of the protective layer 17, and the lubricating layer 18 with a uniform film thickness can be formed on the protective layer 17.

In the present embodiment, it is preferable to heat the substrate 11 on which the lubricating layer 18 is formed. When the heat treatment is performed, the adhesion between the lubricating layer 18 and the protective layer 17 is improved, and the adhesive force between the lubricating layer 18 and the protective layer 17 is improved.

The heat treatment temperature is preferably 100 to 180° C. When the heat treatment temperature is 100° C. or higher, an effect of improving the adhesion between the lubricating layer 18 and the protective layer 17 is sufficiently obtained. In addition, when the heat treatment temperature is 180° C. or lower, it is possible to prevent the thermal decomposition of the lubricating layer 18. The heat treatment time is preferably 10 to 120 minutes.

In the magnetic recording medium 10 of the present embodiment, at least the magnetic layer 16, the protective layer 17, and the lubricating layer 18 are sequentially provided on the substrate 11. In the magnetic recording medium 10 of the present embodiment, the lubricating layer 18 containing the above fluorine-containing ether compound is formed on and in contact with the protective layer 17. The lubricating layer 18 covers the surface of the protective layer 17 with high coverage even if the thickness is thin. Therefore, the lubricating layer 18 in the magnetic recording medium 10 of the present embodiment has excellent wear resistance.

In addition, in the magnetic recording medium 10 of the present embodiment, the lubricating layer 18 covers the surface of the protective layer 17 with high coverage. Therefore, environmental substances that produce contamination substances such as ionic impurities are prevented from entering through voids of the lubricating layer 18. Therefore, the magnetic recording medium 10 of the present embodiment has a small amount of contamination substances present on the surface. In addition, the lubricating layer 18 in the magnetic recording medium 10 of the present embodiment is less likely to generate foreign matter (smear), and can reduce the occurrence of pickup.

Accordingly, the magnetic recording medium 10 of the present embodiment has excellent reliability and durability.

EXAMPLES

Hereinafter, examples of the present invention will be described in more detail with reference to examples and comparative examples. Here, the present invention is not limited only to the following examples.

"Production of Lubricant"

Example 1

The compound represented by Formula (A) was produced by the following method.

First, diallylamine and di-tert-butyl dicarbonate were reacted in methanol to obtain a compound. Next, the obtained compound was oxidized in dichloromethane using meta-chloroperoxybenzoic acid to synthesize a compound represented by the following Formula (20).

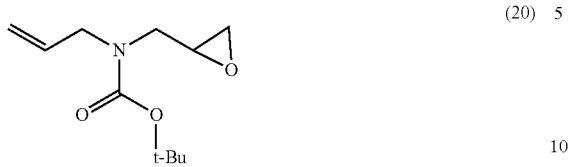

(20)

(in Formula (20), t-Bu represents a tertiary butyl group).

Next, 20 g of a fluoropolyether (a number-average molecular weight of 1,000 and a molecular weight distribution of 1.1) represented by $HOCH_2CF_2O(CF_2CF_2O)_m(CF_2O)_nCF_2CH_2OH$ (in the formula, in which indicates the average degree of polymerization is 4.5, and n which indicates the average degree of polymerization is 4.5), 9.39 g of the compound represented by Formula (20) (a molecular weight of 213.14, 44 mmol), and 20 mL of t-butanol were put into a 200 mL eggplant flask under a nitrogen atmosphere, and stirred at room temperature until the composition became uniform.

0.90 g of potassium tert-butoxide (a molecular weight of 112.21, 8 mmol) was added to the uniform liquid, and the mixture was stirred and reacted at 70° C. for 14 hours. The obtained reaction product was cooled to 25° C. and neutralized with 1 mol/L hydrochloric acid, extracted with Vertrel (registered trademark) XF and washed with water. The organic layer was dehydrated with anhydrous sodium sulfate, the drying agent was filtered off, and the filtrate was then concentrated.

15 mL of trifluoroacetic acid was added to the concentrated filtrate, and the mixture was stirred and reacted at 25° C. for 3 hours. The reaction solution was transferred to a beaker containing 70 mL of 8% sodium bicarbonate water, and extracted twice with 200 mL of ethyl acetate. The organic layer was washed with water and dehydrated with anhydrous sodium sulfate. After the drying agent was filtered off, the filtrate was concentrated, and the residue was purified by silica gel column chromatography to obtain 12.3 g of a compound (A). In Formula (A), ma which indicates the average degree of polymerization is 4.5, and na which indicates the average degree of polymerization is 4.5.

$^1$H-NMR measurement of the obtained compound (A) was performed, and the structure was identified from the following results.

Compound (A); $^1$H-NMR (CD$_3$COCD$_3$);

δ[ppm] 3.4 to 3.9 (18H), 5.1 to 5.2 (2H), 5.2 to 5.3 (2H), 5.8 to 6.0 (2H)

Example 2

The same operation as in Example 1 was performed except that 10.6 g of a compound represented by the following Formula (21) was used in place of the compound represented by Formula (20) to obtain 12.8 g of a compound (B). In Formula (B), mb which indicates the average degree of polymerization is 4.5, and nb which indicates the average degree of polymerization is 4.5.

The compound represented by Formula (21) was synthesized by protecting the amino group of dibutenylamine using di-tert-butyl dicarbonate and oxidizing the double bond.

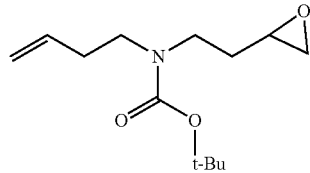

(21)

(in Formula (21), t-Bu represents a tertiary butyl group).

$^1$H-NMR measurement of the obtained compound (B) was performed, and the structure was identified from the following results.

Compound (B); $^1$H-NMR (CD$_3$COCD$_3$);

δ[ppm] 1.6 to 2.0 (4H), 2.2 to 2.4 (4H), 3.4 to 4.0 (18H), 5.0 to 5.1 (2H), 5.1 to 5.2 (2H), 5.8 to 6.0 (2H)

Example 3

The same operation as in Example 1 was performed except that 9.47 g of a compound represented by the following Formula (22) was used in place of the compound represented by Formula (20) to obtain 12.3 g of a compound (C). In Formula (C), mc which indicates the average degree of polymerization is 4.5, and nc which indicates the average degree of polymerization is 4.5.

The compound represented by Formula (22) was synthesized by protecting the amino group of propylamine using di-tert-butyl dicarbonate and reacting it with epibromohydrin.

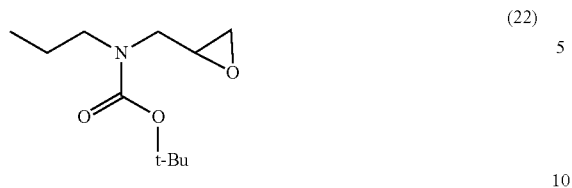

(22)

(in Formula (22), t-Bu represents a tertiary butyl group).

$^1$H-NMR measurement of the obtained compound (C) was performed, and the structure was identified from the following results.

Compound (C); $^1$H-NMR (CD$_3$COCD$_3$);

δ[ppm] 0.8 to 1.0 (6H), 1.5 to 1.6 (4H), 3.3 to 4.2 (18H)

Example 4

The same operation as in Example 1 was performed except that 12.3 g of a compound represented by Formula (23) was used in place of the compound represented by Formula (20) to obtain 13.6 g of a compound (D). In Formula (D), and which indicates the average degree of polymerization is 4.5, and nd which indicates the average degree of polymerization is 4.5.

The compound represented by Formula (23) was synthesized by protecting the amino group of p-anisidine using di-tert-butyl dicarbonate and reacting it with epibromohydrin.

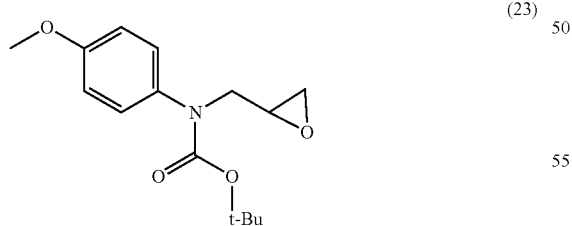

(23)

(in Formula (23), t-Bu represents a tertiary butyl group).

$^1$H-NMR measurement of the obtained compound (D) was performed, and the structure was identified from the following results.

Compound (D); ¹H-NMR (CD₃COCD₃):

δ[ppm] 3.5 to 4.2 (20H), 6.8 to 7.0 (8H)

Example 5

The same operation as in Example 1 was performed except that 17.0 g of a compound represented by Formula (24) was used in place of the compound represented by Formula (20) to obtain 13.7 g of a compound (E). In Formula (E), me which indicates the average degree of polymerization is 4.5, and ne which indicates the average degree of polymerization is 4.5.

The compound represented by Formula (24) was synthesized by protecting the amino group of the compound obtained by the reaction of allylamine and epichlorohydrin using di-tert-butyl dicarbonate and oxidizing the double bond.

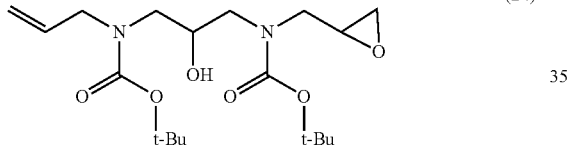

(24)

(in Formula (24), t-Bu represents a tertiary butyl group).

¹H-NMR measurement of the obtained compound (E) was performed, and the structure was identified from the following results.

Compound (E); ¹H-NMR (CD₃COCD₃);

δ[ppm] 3.4 to 3.7 (10H), 3.9 to 4.2 (18H), 5.1 to 5.2 (2H), 5.2 to 5.3 (2H), 5.8 to 6.0 (2H)

Example 6

The same operation as in Example 1 was performed except that 18.2 g of a compound represented by Formula (25) was used in place of the compound represented by Formula (20) to obtain 14.3 g of a compound (F). In Formula (F), mf which indicates the average degree of polymerization is 4.5, and of which indicates the average degree of polymerization is 4.5.

The compound represented by Formula (25) was synthesized by protecting the amino group of the compound obtained by the reaction of 3-butenylamine and epichlorohydrin using di-tert-butyl dicarbonate and oxidizing the double bond.

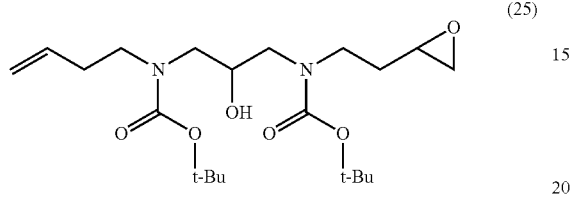

(in Formula (25), t-Bu represents a tertiary butyl group).

$^1$H-NMR measurement of the obtained compound (F) was performed, and the structure was identified from the following results.

Compound (F); $^1$H-NMR (CD$_3$COCD$_3$);

δ[ppm] 1.6 to 2.0 (4H), 2.2 to 2.4 (4H), 3.4 to 4.0 (28H), 5.0 to 5.1 (2H), 5.1 to 5.2 (2H), 5.8 to 6.0 (2H)

Example 7

The compound represented by Formula (G) was produced by the following method.

20.0 g of a fluoropolyether (a number-average molecular weight of 1,000 and a molecular weight distribution of 1.1) represented by HOCH$_2$CF$_2$O(CF$_2$CF$_2$O)$_m$(CF$_2$O)$_n$CF$_2$CH$_2$OH (in the formula, m which indicates the average degree of polymerization is 4.5, and n which indicates the average degree of polymerization is 4.5), 2.56 g of the compound represented by Formula (20), and 12 mL of t-butanol were put into a 100 mL eggplant flask under a nitrogen gas atmosphere, and stirred at room temperature until the composition became uniform. Then, 0.674 g of potassium tert-butoxide was added to the uniform liquid, and the mixture was stirred and reacted at 70° C. for 8 hours to obtain a reaction product.

The obtained reaction product was cooled to 25° C., neutralized with 0.5 mol/L of hydrochloric acid, and then extracted with Vertrel (registered trademark) XF, and the organic layer was washed with water and dehydrated with anhydrous sodium sulfate. After the drying agent was filtered off, the filtrate was concentrated, and the residue was purified by silica gel column chromatography to obtain 9.71 g of a compound represented by the following Formula (26).

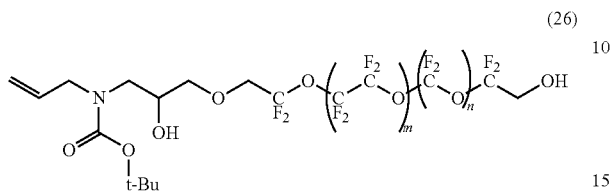

(26)

(in Formula (26), m which indicates the average degree of polymerization is 4.5, and n which indicates the average degree of polymerization is 4.5; and t-Bu represents a tertiary butyl group).

6.07 g of a compound represented by Formula (26), 1.21 g of a compound represented by the following Formula (27), and 50 mL of t-butanol were put into a 200 mL eggplant flask under a nitrogen gas atmosphere, and stirred at room temperature until the composition became uniform. 0.168 g of potassium tert-butoxide was added to the uniform liquid, and the mixture was stirred and reacted at 70° C. for 16 hours.

The compound represented by Formula (27) was synthesized by reacting a compound in which the hydroxy group on one side of ethylene glycol was protected using dihydropyran with epibromohydrin.

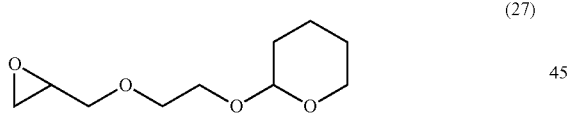

(27)

The temperature of the liquid after the reaction was completed was returned to room temperature, 20 g of a 10% hydrogen chloride/methanol solution (hydrogen chloride-methanol reagent (5-10%) commercially available from Tokyo Chemical Industry Co., Ltd.) was added, and the mixture was stirred at room temperature for 1 hour. The reaction solution was transferred to a beaker containing 70 mL of 8% sodium bicarbonate water, and extracted twice with 200 mL of ethyl acetate. The organic layer was washed with water and dehydrated with anhydrous sodium sulfate, the drying agent was filtered off, and the filtrate was then concentrated.

15 mL of trifluoroacetic acid was added to the concentrated filtrate, and the mixture was stirred and reacted at 25°

C. for 3 hours. The reaction solution was transferred to a beaker containing 70 mL of 8% sodium bicarbonate water, and extracted twice with 200 mL of ethyl acetate. The organic layer was washed with water and dehydrated with anhydrous sodium sulfate. After the drying agent was filtered off, the filtrate was concentrated, and the residue was purified by silica gel column chromatography to obtain 4.31 g of a compound (G). In Formula (G), mg which indicates the average degree of polymerization is 4.5, and ng which indicates the average degree of polymerization is 4.5.

$^1$H-NMR measurement of the obtained compound (G) was performed, and the structure was identified from the following results.

Compound (G); $^1$H-NMR (CD$_3$COCD$_3$);

δ[ppm] 3.4 to 4.2 (29H), 5.1 to 5.2 (1H), 5.2 to 5.3 (1H), 5.8 to 6.0 (1H)

Example 8

The same operation as in Example 7 was performed except that the compound represented by Formula (21) was used in place of the compound represented by Formula (20), and via the intermediate represented by Formula (28), 4.41 g of a compound (H) was obtained. In Formula (H), mh which indicates the average degree of polymerization is 4.5, and nh which indicates the average degree of polymerization is 4.5.

(28)

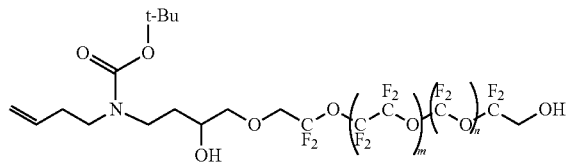

(in Formula (28), m which indicates the average degree of polymerization is 4.5, and n which indicates the average degree of polymerization is 4.5; and t-Bu represents a tertiary butyl group).

$^1$H-NMR measurement of the obtained compound (H) was performed, and the structure was identified from the following results.

Compound (H); $^1$H-NMR (CD$_3$COCD$_3$);

δ[ppm] 1.6 to 2.0 (2H), 2.2 to 2.4 (2H), 3.4 to 4.0 (20H), 5.0 to 5.1 (1H), 5.1 to 5.2 (1H), 5.8 to 6.0 (1H)

Example 9

The same operation as in Example 7 was performed except that the compound represented by Formula (22) was used in place of the compound represented by Formula (20), and via the intermediate represented by Formula (29), 4.32 g of a compound (I) was obtained. In Formula (I), mi which indicates the average degree of polymerization is 4.5, and ni which indicates the average degree of polymerization is 4.5.

(29)

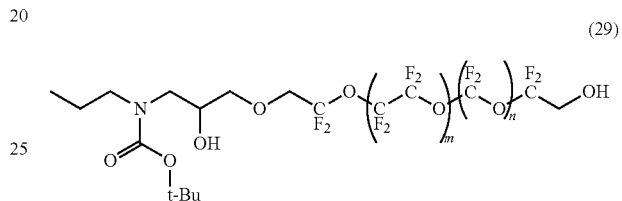

(in Formula (29), m which indicates the average degree of polymerization is 4.5, and n which indicates the average degree of polymerization is 4.5; and t-Bu represents a tertiary butyl group).

$^1$H-NMR measurement of the obtained compound (1) was performed, and the structure was identified from the following results.

Compound (I); $^1$H-NMR (CD$_3$COCD$_3$);

δ[ppm] 0.8 to 1.0 (3H), 1.5 to 1.6 (2H), 3.3 to 4.2 (20H)

Example 10

The same operation as in Example 7 was performed except that the compound represented by Formula (23) was used in place of the compound represented by Formula (20), and via the intermediate represented by Formula (30), 4.57 g of a compound (J) was obtained. In Formula (J), mj which indicates the average degree of polymerization is 4.5, and nj which indicates the average degree of polymerization is 4.5.

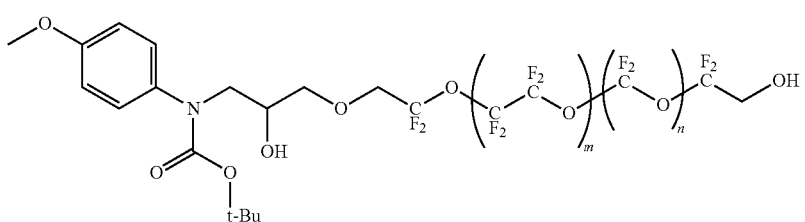

(30)

(in Formula (30), m which indicates the average degree of polymerization is 4.5, and n which indicates the average degree of polymerization is 4.5; and t-Bu represents a tertiary butyl group).

$^1$H-NMR measurement of the obtained compound (J) was performed, and the structure was identified from the following results.

Compound (J); $^1$H-NMR (CD$_3$COCD$_3$);

δ[ppm] 3.5 to 4.2 (21H), 6.8 to 7.0 (4H)

Example 11

The same operation as in Example 7 was performed except that the compound represented by Formula (24) was used in place of the compound represented by Formula (20), and via the intermediate represented by Formula (31), 4.57 g of a compound (K) was obtained. In Formula (K), mk which indicates the average degree of polymerization is 4.5, and nk which indicates the average degree of polymerization is 4.5.

(in Formula (31), m which indicates the average degree of polymerization is 4.5, and n which indicates the average degree of polymerization is 4.5; and t-Bu represents a tertiary butyl group).

$^1$H-NMR measurement of the obtained compound (K) was performed, and the structure was identified from the following results.

Compound (K); $^1$H-NMR (CD$_3$COCD$_1$);

δ[ppm] 3.4 to 3.7 (9H), 3.9 to 4.2 (16H), 5.1 to 5.2 (1H), 5.2 to 5.3 (1H), 5.8 to 6.0 (1H)

Example 12

The same operation as in Example 7 was performed except that the compound represented by Formula (25) was used in place of the compound represented by Formula (20), and via the intermediate represented by Formula (32), 4.67 g of a compound (L) was obtained. In Formula (L), ml which indicates the average degree of polymerization is 4.5, and nl which indicates the average degree of polymerization is 4.5.

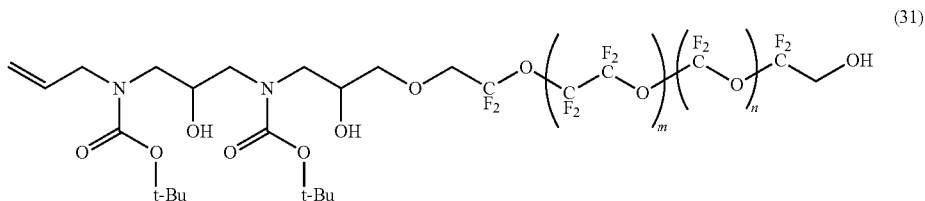

(31)

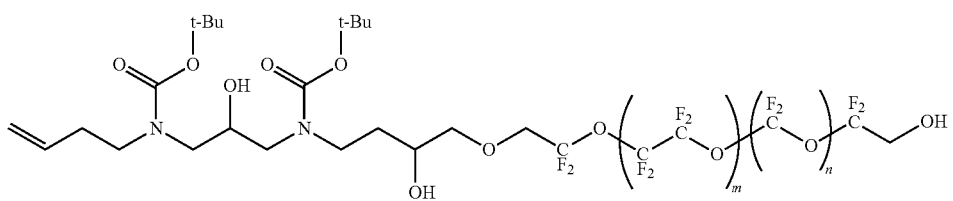
(32)

(in Formula (32), m which indicates the average degree of polymerization is 4.5, and n which indicates the average degree of polymerization is 4.5; and t-Bu represents a tertiary butyl group).

$^1$H-NMR measurement of the obtained compound (L) was performed, and the structure was identified from the following results.

Compound (L); $^1$H-NMR (CD$_3$COCD$_3$);

δ[ppm] 1.6 to 2.0 (2H), 2.2 to 2.4 (2H), 3.4 to 4.0 (25H), 5.0 to 5.1 (1H), 5.1 to 5.2 (1H), 5.8 to 6.0 (1H)

Example 13

The same operation as in Example 7 was performed except that the compound represented by Formula (24) was used in place of the compound represented by Formula (20) and a compound represented by Formula (33) was used in place of the compound represented by Formula (27), and via the intermediate represented by Formula (31), 4.62 g of a compound (M) was obtained. In Formula (M), mm which indicates the average degree of polymerization is 4.5, and nm which indicates the average degree of polymerization is 4.5.

The compound represented by Formula (33) was synthesized by reacting a compound in which the hydroxy group on one side of 1,3-propanediol was protected using dihydropyran with epibromohydrin.

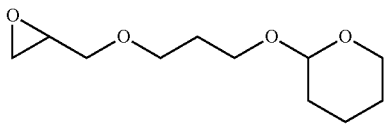
(33)

$^1$H-NMR measurement of the obtained compound (M) was performed, and the structure was identified from the following results.

Compound (M); 1H-NMR (CD$_3$COCD$_3$);

δ[ppm] 1.6 to 2.0 (2H), 3.4 to 3.7 (9H), 3.9 to 4.2 (16H), 5.1 to 5.2 (1H), 5.2 to 5.3 (1H), 5.8 to 6.0 (1H)

Example 14

The compound represented by Formula (N) was produced by the following method.

In the same manner as in Example 7, 9.71 g of the compound represented by Formula (26) was obtained.

6.07 g of the compound represented by Formula (26), 1.64 g of a compound represented by the following Formula (34), and 50 mL of t-butanol were put into a 200 mL eggplant flask under a nitrogen gas atmosphere, and stirred at room temperature until the composition became uniform. 0.168 g of potassium tert-butoxide was added to the uniform liquid, and the mixture was stirred and reacted at 70° C. for 16 hours.

The compound represented by Formula (34) was synthesized by reacting a compound represented by the following Formula (35), in which the hydroxy group of 2-aminoethanol was protected with methyl tert-butyl ether and the amino group was protected with di-tert-butyl dicarbonate, with epibromohydrin.

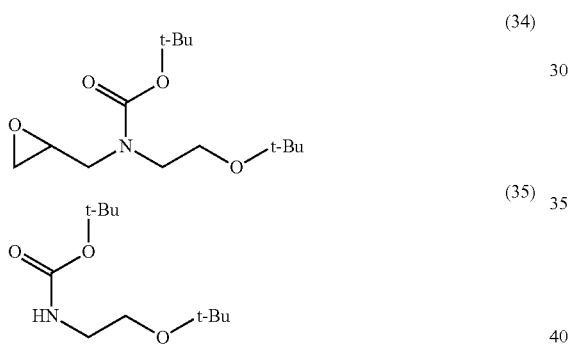

(in Formula (34) and Formula (35), t-Bu represents a tertiary butyl group).

The temperature of the liquid after the reaction was completed was returned to room temperature, 20 g of a 10% hydrogen chloride/methanol solution (hydrogen chloride-methanol reagent (5-10%) commercially available from Tokyo Chemical Industry Co., Ltd.) was added, and the mixture was stirred at room temperature for 1 hour. The reaction solution was transferred to a beaker containing 70 mL of 8% sodium bicarbonate water, and extracted twice with 200 mL of ethyl acetate. The organic layer was washed with water and dehydrated with anhydrous sodium sulfate, the drying agent was filtered off, and the filtrate was then concentrated.

15 mL of trifluoroacetic acid was added to the concentrated filtrate, and the mixture was stirred and reacted at 25° C. for 3 hours. The reaction solution was transferred to a beaker containing 70 mL of 8% sodium bicarbonate water, and extracted twice with 200 mL of ethyl acetate. The organic layer was washed with water and dehydrated with anhydrous sodium sulfate. After the drying agent was filtered off, the filtrate was concentrated, and the residue was purified by silica gel column chromatography to obtain 4.31 g of a compound (N). In Formula (N), nm which indicates the average degree of polymerization is 4.5, and nn which indicates the average degree of polymerization is 4.5.

$^1$H-NMR measurement of the obtained compound (N) was performed, and the structure was identified from the following results.

Compound (N); $^1$H-NMR (CD$_3$COCD$_3$);

δ[ppm] 3.4 to 4.2 (29H), 5.1 to 5.2 (1H), 5.2 to 5.3 (1H), 5.8 to 6.0 (1H)

Example 15

The same operation as in Example 14 was performed except that the compound represented by Formula (21) was used in place of the compound represented by Formula (20), and via the intermediate represented by Formula (28), 4.41 g of a compound (O) was obtained. In Formula (O), mo which indicates the average degree of polymerization is 4.5, and no which indicates the average degree of polymerization is 4.5.

$^1$H-NMR measurement of the obtained compound (O) was performed, and the structure was identified from the following results.

Compound (O); $^1$H-NMR (CD$_3$COCD$_3$);

δ[ppm] 1.6 to 2.0 (2H), 2.2 to 2.4 (2H), 3.4 to 4.0 (20H), 5.0 to 5.1 (1H), 5.1 to 5.2 (1H), 5.8 to 6.0 (1H)

Example 16

The same operation as in Example 14 was performed except that the compound represented by Formula (22) was used in place of the compound represented by Formula (20), and via the intermediate represented by Formula (29), 4.32 g of a compound (P) was obtained. In Formula (P), mp which indicates the average degree of polymerization is 4.5, and np which indicates the average degree of polymerization is 4.5.

$^1$H-NMR measurement of the obtained compound (P) was performed, and the structure was identified from the following results.

Compound (P); $^1$H-NMR (CD$_3$COCD$_3$);

δ[ppm] 0.8 to 1.0 (3H), 1.5 to 1.6 (2H), 3.3 to 4.2 (20H)

Example 17

The same operation as in Example 14 was performed except that the compound represented by Formula (23) was used in place of the compound represented by Formula (20), and via the intermediate represented by Formula (30), 4.57 g of a compound (Q) was obtained. In Formula (Q), mq which indicates the average degree of polymerization is 4.5, and nq which indicates the average degree of polymerization is 4.5.

$^1$H-NMR measurement of the obtained compound (Q) was performed, and the structure was identified from the following results.

Compound (Q); $^1$H-NMR (CD$_3$COCD$_3$);

δ[ppm] 3.5 to 4.2 (21H), 6.8 to 7.0 (4H)

Example 18

The same operation as in Example 14 was performed except that a compound represented by Formula (36) was used in place of the compound represented by Formula (20), and via the intermediate represented by Formula (37), 4.57 g of a compound (R) was obtained. In Formula (R), mr which indicates the average degree of polymerization is 4.5, and nr which indicates the average degree of polymerization is 4.5.

The compound represented by Formula (36) was synthesized by protecting the hydroxy group of 1,3-diallyloxy-2-propanol using dihydropyran and oxidizing the double bond.

(36)
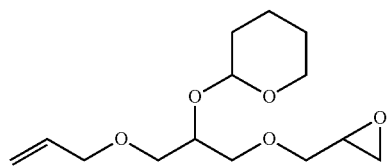
(37)
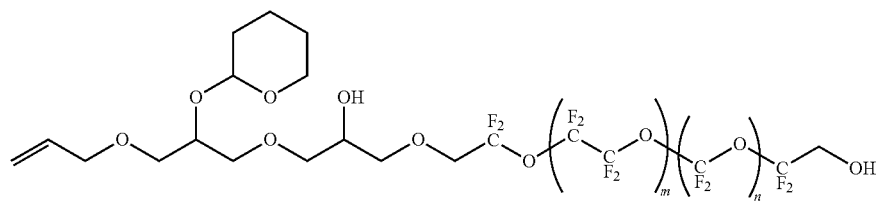

(in Formula (37), in which indicates the average degree of polymerization is 4.5, and n which indicates the average degree of polymerization is 4.5).

$^1$H-NMR measurement of the obtained compound (R) was performed, and the structure was identified from the following results.

Compound (R); $^1$H-NMR (CD$_3$COCD$_3$);

δ[ppm] 3.4 to 3.7 (9H), 3.9 to 4.2 (16H), 5.1 to 5.2 (1H), 5.2 to 5.3 (1H), 5.8 to 6.0 (1H)

Example 19

The same operation as in Example 14 was performed except that the compound represented by Formula (24) was used in place of the compound represented by Formula (20), and via the intermediate represented by Formula (31), 4.57 g of a compound (S) was obtained. In Formula (S), ms which indicates the average degree of polymerization is 4.5, and ns which indicates the average degree of polymerization is 4.5.

$^1$H-NMR measurement of the obtained compound (S) was performed, and the structure was identified from the following results.

Compound (S); $^1$H-NMR (CD$_3$COCD$_3$);

δ[ppm] 3.4 to 3.7 (9H), 3.9 to 4.2 (16H), 5.1 to 5.2 (1H), 5.2 to 5.3 (1H), 5.8 to 6.0 (1H)

Example 20

The same operation as in Example 14 was performed except that the compound represented by Formula (25) was used in place of the compound represented by Formula (20), and via the intermediate represented by Formula (32), 4.67 g of a compound (T) was obtained. In Formula (T), mt which indicates the average degree of polymerization is 4.5, and nt which indicates the average degree of polymerization is 4.5.

$^1$H-NMR measurement of the obtained compound (T) was performed, and the structure was identified from the following results.

Compound (T); $^1$H-NMR (CD$_3$COCD$_3$);

δ[ppm] 1.6 to 2.0 (2H), 2.2 to 2.4 (2H), 3.4 to 4.0 (25H), 5.0 to 5.1 (1H), 5.1 to 5.2 (1H), 5.8 to 6.0 (1H)

Example 21

The compound represented by Formula (U) was produced by the following method.

In the same manner as in Example 18, 10.2 g of the compound represented by Formula (37) was obtained.

6.37 g of the compound represented by Formula (37), 2.68 g of a compound represented by the following Formula (38), and 50 mL of t-butanol were put into a 200 mL eggplant flask under a nitrogen gas atmosphere, and stirred at room temperature until the composition became uniform. 0.168 g of potassium tert-butoxide was added to the uniform liquid, and the mixture was stirred and reacted at 70° C. for 16 hours.

The compound represented by Formula (38) was synthesized by reacting a compound represented by the following Formula (39), which was synthesized by protecting the amino group of diallylamine with di-tert-butyl dicarbonate and oxidizing the double bond, with the compound represented by Formula (35).

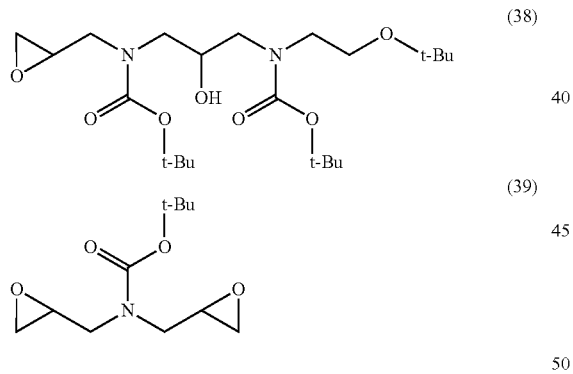

(in Formula (38) and Formula (39), t-Bu represents a tertiary butyl group).

The temperature of the liquid after the reaction was completed was returned to room temperature, 20 g of a 10% hydrogen chloride/methanol solution (hydrogen chloride-methanol reagent (5-10%) commercially available from Tokyo Chemical Industry Co., Ltd.) was added, and the mixture was stirred at room temperature for 1 hour. The reaction solution was transferred to a beaker containing 70 mL of 8% sodium bicarbonate water, and extracted twice with 200 mL of ethyl acetate. The organic layer was washed with water and dehydrated with anhydrous sodium sulfate, the drying agent was filtered off, and the filtrate was then concentrated.

20 mL of trifluoroacetic acid was added to the concentrated filtrate, and the mixture was stirred and reacted at 25° C. for 3 hours. The reaction solution was transferred to a beaker containing 70 mL of 8% sodium bicarbonate water, and extracted twice with 200 mL of ethyl acetate. The organic layer was washed with water and dehydrated with anhydrous sodium sulfate. After the drying agent was filtered off, the filtrate was concentrated, and the residue was purified by silica gel column chromatography to obtain 4.83 g of a compound (U). In Formula (U), mu which indicates the average degree of polymerization is 4.5, and nu which indicates the average degree of polymerization is 4.5.

$^1$H-NMR measurement of the obtained compound (U) was performed, and the structure was identified from the following results.

Compound (U); $^1$H-NMR ($CD_3COCD_3$);

δ[ppm] 3.4 to 3.9 (25H), 5.1 to 5.2 (1H), 5.2 to 5.3 (1H), 5.8 to 6.0 (1H)

Example 22

The same operation as in Example 21 was performed except that the compound represented by Formula (24) was used in place of the compound represented by Formula (36), and via the intermediate represented by Formula (31), 4.67 g of a compound (V) was obtained. In Formula (V), my which indicates the average degree of polymerization is 4.5, and nv which indicates the average degree of polymerization is 4.5.

$^1$H-NMR measurement of the obtained compound (V) was performed, and the structure was identified from the following results.

Compound (V); $^1$H-NMR ($CD_3COCD_3$);

δ[ppm] 3.4 to 3.9 (25H), 5.1 to 5.2 (1H), 5.2 to 5.3 (1H), 5.8 to 6.0 (1H)

Example 23

The same operation as in Example 21 was performed except that the compound represented by Formula (25) was used in place of the compound represented by Formula (36), and via the intermediate represented by Formula (32), 4.92 g of a compound (W) was obtained. In Formula (W), mw which indicates the average degree of polymerization is 4.5, and nw which indicates the average degree of polymerization is 4.5.

$^1$H-NMR measurement of the obtained compound (W) was performed, and the structure was identified from the following results.

Compound (W); $^1$H-NMR ($CD_3COCD_3$);

δ[ppm] 1.6 to 2.0 (2H), 2.2 to 2.4 (2H), 3.4 to 4.0 (25H), 5.0 to 5.1 (1H), 5.1 to 5.2 (1H), 5.8 to 6.0 (1H)

Example 24

The same operation as in Example 14 was performed except that a fluoropolyether represented by $HOCH_2CF_2O(CF_2CF_2O)_xCF_2CH_2OH$ (in the formula, x which indicates the average degree of polymerization is 7.0) was used in place of a fluoropolyether represented by $HOCH_2CF_2O(CF_2CF_2O)_m(CF_2O)_nCF_2CH_2OH$ (in the formula, m which indicates the average degree of polymerization is 4.5, and n which indicates the average degree of polymerization is 4.5), and the compound represented by Formula (24) was used in place of the compound represented by Formula (20), and via the intermediate represented by Formula (40), 4.53 g of a compound (X) was obtained. In Formula (X), x which indicates the average degree of polymerization is 7.0.

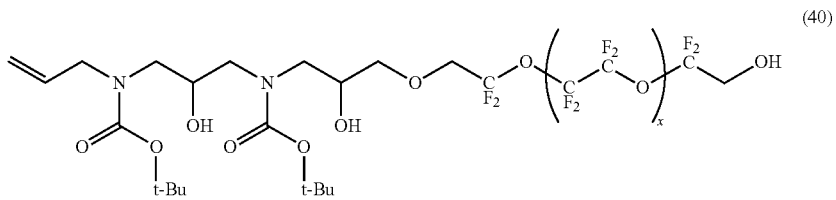

(40)

(in Formula (40), x which indicates the average degree of polymerization is 7.0; and t-Bu represents a tertiary butyl group).

$^1$H-NMR measurement of the obtained compound (X) was performed, and the structure was identified from the following results.

Compound (X); $^1$H-NMR (CD$_3$COCD$_3$);

δ[ppm] 3.4 to 3.7 (9H), 3.9 to 4.2 (16H), 5.1 to 5.2 (1H), 5.2 to 5.3 (1H), 5.8 to 6.0 (1H)

Example 25

The same operation as in Example 14 was performed except that a fluoropolyether represented by HOCH$_2$CF(CF$_3$)(OCF(CF$_3$)CF$_2$)$_y$OCF(CF$_3$)CH$_2$OH (in the formula, y which indicates the average degree of polymerization is 4.5) was used in place of a fluoropolyether represented by HOCH$_2$CF$_2$O(CF$_2$CF$_2$O)$_m$(CF$_2$O)$_n$CF$_2$CH$_2$OH (in the formula, m which indicates the average degree of polymerization is 4.5, and n which indicates the average degree of polymerization is 4.5), and the compound represented by Formula (24) was used in place of the compound represented by Formula (20), and via the intermediate represented by Formula (41), 4.66 g of a compound (Y) was obtained. In Formula (Y), y which indicates the average degree of polymerization is 4.5.

(in Formula (41), y which indicates the average degree of polymerization is 4.5; and t-Bu represents a tertiary butyl group).

$^1$H-NMR measurement of the obtained compound (Y) was performed, and the structure was identified from the following results.

Compound (Y); $^1$H-NMR (CD$_3$COCD$_3$);

δ[ppm] 3.4 to 3.7 (9H), 3.9 to 4.2 (16H), 5.1 to 5.2 (1H), 5.2 to 5.3 (1H), 5.8 to 6.0 (1H)

Example 26

The same operation as in Example 14 was performed except that a fluoropolyether represented by HOCH$_2$CF$_2$CF$_2$O(CF$_2$CF$_2$CF$_2$O)$_z$CF$_2$CF$_2$CH$_2$OH (in the formula, z which indicates the average degree of polymerization is 4.5) was used in place of a fluoropolyether represented by HOCH$_2$CF$_2$O(CF$_2$CF$_2$O)$_m$(CF$_2$O)$_n$CF$_2$CH$_2$OH (in the formula, m which indicates the average degree of polymerization is 4.5, and n which indicates the average degree of polymerization is 4.5), and the compound represented by Formula (24) was used in place of the compound represented by Formula (20), and via the intermediate represented by Formula (42), 4.66 g of a compound (Z) was obtained. In Formula (Z), z which indicates the average degree of polymerization is 4.5.

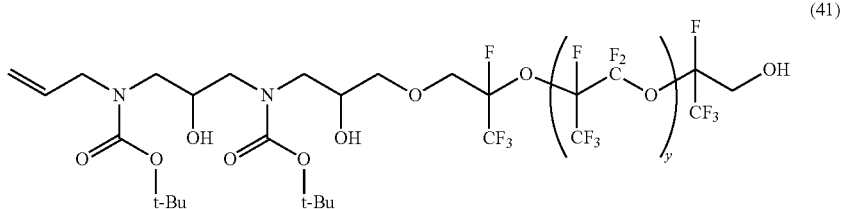

(41)

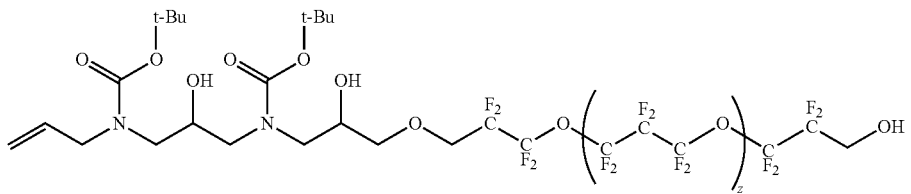

(42)

(in Formula (42), z which indicates the average degree of polymerization is 4.5; and t-Bu represents a tertiary butyl group).

$^1$H-NMR measurement of the obtained compound (Z) was performed, and the structure was identified from the following results.

Compound (Z); $^1$H-NMR (CD$_3$COCD$_3$);

δ[ppm] 3.4 to 3.7 (9H), 3.9 to 4.2 (16H), 5.1 to 5.2 (1H), 5.2 to 5.3 (1H), 5.8 to 6.0 (1H)

Table 1 shows the structure of R$^1$, the structure of R$^2$ (in Formula (2), a and X in [A], and b, c, and X in [B]), the structure of R$^3$, the structure of R$^4$ (in Formula (3), d and X in [C], and e, f, and X in [D]), and the structure of R$^5$, when the compounds of Examples 1 to 26 obtained in this manner were applied to Formula (1), and the total number of hydroxy groups [—OH] and secondary amine structures [—NH-] contained in the molecule.

TABLE 1

| Compound | R¹ | R² [A] | R² [B] | R³ | R⁴ [C] | R⁴ [D] | R⁵ | Total number of [—NH—] and [—OH—] |
|---|---|---|---|---|---|---|---|---|
| Example 1 | (A) | allyl group | a = 1, X = NH | — | Formula (8) | d = 1, X = NH | — | same as R¹ | 4 |
| Example 2 | (B) | butenyl group | — | b = 1, c = 2, X = NH | Formula (8) | — | e = 1, f = 2, X = NH | same as R¹ | 4 |
| Example 3 | (C) | propyl group | a = 1, X = NH | — | Formula (8) | d = 1, X = NH | — | same as R¹ | 4 |
| Example 4 | (D) | methoxyphenyl group | a = 1, X = NH | — | Formula (8) | d = 1, X = NH | — | same as R¹ | 4 |
| Example 5 | (E) | allyl group | a = 2, X = NH | — | Formula (8) | d = 2, X = NH | — | same as R¹ | 8 |
| Example 6 | (F) | butenyl group | a = 1, X = NH | b = 1, c = 2, X = NH | Formula (8) | d = 1, X = NH | e = 1, f = 2, X = NH | same as R¹ | 8 |
| Example 7 | (G) | allyl group | a = 1, X = NH | — | Formula (8) | d = 1, X = O | — | hydroxyethyl group | 4 |
| Example 8 | (H) | butenyl group | — | b = 1, c = 2, X = NH | Formula (8) | d = 1, X = O | — | hydroxyethyl group | 4 |
| Example 9 | (I) | propyl group | a = 1 X = NH | — | Formula (8) | d = 1, X = O | — | hydroxyethyl group | 4 |
| Example 10 | (J) | methoxyphenyl group | a = 1, X = NH | — | Formula (8) | d = 1, X = O | — | hydroxyethyl group | 4 |
| Example 11 | (K) | allyl group | a = 2, X = NH | — | Formula (8) | d = 1, X = O | — | hydroxyethyl group | 6 |
| Example 12 | (L) | butenyl group | a = 1, X = NH | b = 1, c = 2, X = NH | Formula (8) | d = 1, X = O | — | hydroxyethyl group | 6 |
| Example 13 | (M) | allyl group | a = 2, X = NH | — | Formula (8) | d = 1, X = O | — | hydroxypropyl group | 6 |
| Example 14 | (N) | allyl group | a = 1, X = NH | — | Formula (8) | d = 1, X = NH | — | hydroxyethyl group | 5 |
| Example 15 | (O) | butenyl group | — | b = 1, c = 2, X = NH | Formula (8) | d = 1, X = NH | — | hydroxyethyl group | 5 |
| Example 16 | (P) | propyl group | a = 1, X = NH | — | Formula (8) | d = 1, X = NH | — | hydroxyethyl group | 5 |
| Example 17 | (Q) | methoxyphenyl group | a = 1, X = NH | — | Formula (8) | d = 1, X = NH | — | hydroxyethyl group | 5 |
| Example 18 | (R) | allyl group | a = 2, X = O | — | Formula (8) | d = 1, X = NH | — | hydroxyethyl group | 5 |
| Example 19 | (S) | allyl group | a = 2, X = NH | — | Formula (8) | d = 1, X = NH | — | hydroxyethyl group | 7 |
| Example 20 | (T) | butenyl group | a = 1, X = NH | b = 1, c = 2, X = NH | Formula (8) | d = 1, X = NH | — | hydroxyethyl group | 7 |
| Example 21 | (U) | allyl group | a = 2, X = O | — | Formula (8) | d = 2, X = NH | — | hydroxyethyl group | 7 |
| Example 22 | (V) | allyl group | a = 2, X = NH | — | Formula (8) | d = 2, X = NH | — | hydroxyethyl group | 9 |
| Example 23 | (W) | butenyl group | a = 1, X = NH | b = 1, c = 2, X = NH | Formula (8) | d = 2, X = NH | — | hydroxyethyl group | 9 |
| Example 24 | (X) | allyl group | a = 2, X = NH | — | Formula (8) | d = 1, X = NH | — | hydroxyethyl group | 7 |
| Example 25 | (Y) | allyl group | a = 2, X = NH | — | Formula (9) | d = 1, X = NH | — | hydroxyethyl group | 7 |
| Example 26 | (Z) | allyl group | a = 2, X = NH | — | Formula (10) | d = 1, X = NH | — | hydroxyethyl group | 7 |

Comparative Example 1

The compound represented by the following Formula (AA) was synthesized by the method described in Patent Document 3.

(AA)

(in Formula (AA), jA which indicates the average degree of polymerization is 4.5, and kA which indicates the average degree of polymerization is 4.5).

Comparative Example 2

The compound represented by the following Formula (AB) was synthesized by the method described in Patent Document 1.

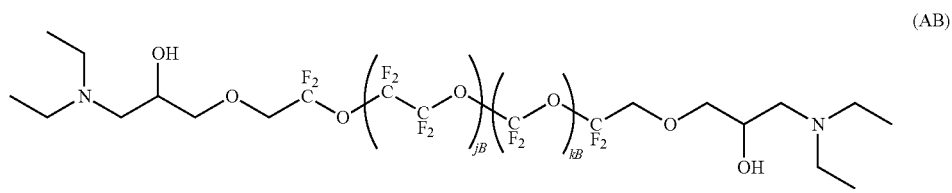

(AB)

(in Formula (AB), jB which indicates the average degree of polymerization is 4.5, and kB which indicates the average degree of polymerization is 4.5).

Comparative Example 3

The compound represented by the following Formula (AC) was synthesized by the method described in Patent Document 2.

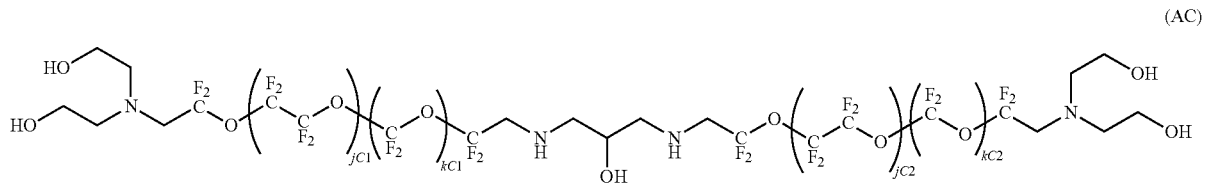

(AC)

(in Formula (AC), jC1, kC1, jC2, and kC2 which indicate average degrees of polymerization are 4.5).

Table 2 and Table 3 show the number-average molecular weight (Mn) of the compounds of Examples 1 to 26 and Comparative Examples 1 to 3 obtained in this manner.

TABLE 2

| | Number-average molecular weight | Compound | Film thickness (Å) | Friction coefficient increase time (Sec) |
|---|---|---|---|---|
| Example 1 | 1228 | A | 9.0 | A |
| Example 2 | 1284 | B | 9.0 | A |
| Example 3 | 1232 | C | 9.0 | B |
| Example 4 | 1360 | D | 9.0 | A |
| Example 5 | 1374 | E | 9.0 | B |
| Example 6 | 1430 | F | 9.0 | B |
| Example 7 | 1233 | G | 9.0 | B |
| Example 8 | 1261 | H | 9.0 | B |
| Example 9 | 1235 | I | 9.0 | B |
| Example 10 | 1305 | J | 9.0 | B |
| Example 11 | 1306 | K | 9.0 | A |
| Example 12 | 1334 | L | 9.0 | A |
| Example 13 | 1320 | M | 9.0 | A |
| Example 14 | 1232 | N | 9.0 | A |
| Example 15 | 1260 | O | 9.0 | A |

TABLE 3

| | Number-average molecular weight | Compound | Film thickness (Å) | Friction coefficient increase time (Sec) |
|---|---|---|---|---|
| Example 16 | 1234 | P | 9.0 | A |
| Example 17 | 1304 | Q | 9.0 | A |
| Example 18 | 1307 | R | 9.0 | B |
| Example 19 | 1305 | S | 9.0 | A |
| Example 20 | 1332 | T | 9.0 | A |
| Example 21 | 1380 | U | 9.0 | B |
| Example 22 | 1378 | V | 9.0 | B |
| Example 23 | 1406 | W | 9.0 | B |
| Example 24 | 1295 | X | 9.0 | A |
| Example 25 | 1330 | Y | 9.0 | A |
| Example 26 | 1330 | Z | 9.0 | A |
| Comparative Example 1 | 1266 | AA | 9.0 | C |
| Comparative Example 2 | 1260 | AB | 9.0 | D |
| Comparative Example 3 | 1232 | AC | 9.0 | D |

Next, solutions for forming a lubricating layer were prepared using the compounds obtained in Examples 1 to 26 and Comparative Examples 1 to 3 by the following method. Then, a lubricating layer of a magnetic recording medium was formed using the obtained solution for forming a lubricating layer by the following method to obtain magnetic recording media of Examples 1 to 26 and Comparative Examples 1 to 3.

"Solution for Forming Lubricating Layer"

The compounds obtained in Examples 1 to 26 and Comparative Examples 1 to 3 were dissolved in Vertrel (registered trademark) XF and diluted with Vertrel (registered trademark) XF such that the film thickness became 9 Å when applied onto the protective layer, and used as solutions for forming a lubricating layer.

"Magnetic Recording Medium"

A magnetic recording medium in which an adhesive layer, a soft magnetic layer, a first underlayer, a second underlayer, a magnetic layer, and a protective layer were sequentially provided on a substrate having a diameter of 65 mm was prepared. The protective layer was made of carbon.

The solutions for forming a lubricating layer of Examples 1 to 26 and Comparative Examples 1 to 3 were applied onto the protective layer of the magnetic recording medium, in which respective layers up to the protective layer were formed, by a dipping method. Here, the dipping method was performed under conditions of an immersion speed of 10 mm/sec, an immersion time of 30 sec, and a lifting speed of 1.2 mm/sec.

Then, the magnetic recording medium to which the solution for forming a lubricating layer was applied was put into a thermostatic chamber at 120° C. and heated for 10 minutes to remove the solvent in the solution for forming a lubricating layer, and thus the lubricating layer was formed on the protective layer to obtain a magnetic recording medium.

The film thickness of the lubricating layer of the magnetic recording media of Examples 1 to 26 and Comparative Examples 1 to 3 obtained in this manner was measured using FT-IR (product name: Nicolet iS50, commercially available from Thermo Fisher Scientific). The results are shown in Table 2 and Table 3.

Next, the following wear resistance test was performed on the magnetic recording media of Examples 1 to 26 and Comparative Examples 1 to 3.

(Wear Resistance Test)

Using a pin-on disc-type friction wear tester, an alumina sphere having a diameter of 2 mm as a contact was slid on the lubricating layer of the magnetic recording medium at a load of 40 gf and a sliding speed of 0.25 m/sec, and the friction coefficient of the surface of the lubricating layer was measured. Then, the sliding time until the friction coefficient of the surface of the lubricating layer rapidly increased was measured. The sliding time until the friction coefficient rapidly increased was measured four times for the lubricating layer of each magnetic recording medium, and the average value (time) thereof was used as an index of the wear resistance of a lubricant coating.

Table 2 and Table 3 show the results of the magnetic recording media using the compounds of Examples 1 to 26 and the compounds of Comparative Examples 1 to 3. The friction coefficient increase time was evaluated as follows. Here, it is understood that a larger value of the friction coefficient increase time indicates better results.

A (excellent): 650 sec or longer

B (good): 550 sec or longer and shorter than 650 sec

C (acceptable): 450 sec or longer and shorter than 550 sec

D (unacceptable): shorter than 450 sec

Here, the time until the friction coefficient rapidly increased could be used as an index of the wear resistance of the lubricating layer for the following reasons. This is because wear of the lubricating layer of the magnetic recording medium proceeds when the magnetic recording medium is used, and when the lubricating layer disappears due to wear, the contact and the protective layer come into direct contact with each other, and the friction coefficient rapidly increases. The time until the friction coefficient rapidly increases is thought to be correlated with the friction test.

As shown in Table 3, the magnetic recording media of Examples 1 to 26 had a longer sliding time until the friction coefficient rapidly increased and better wear resistance than the magnetic recording media of Comparative Examples 1 to 3. This is speculated to be because, in the magnetic recording media of Examples 1 to 26, in the fluorine-containing ether compound represented by Formula (1) forming a lubricating layer, a linking group containing a hydroxy group and a secondary amine structure was disposed between one or both terminal groups and a perfluoropolyether chain.

In particular, in Examples 1, 2, 4, 11 to 17, 19, 20, and 24 to 26 using the compounds (A), (B), (D), (K) to (Q), (S), (T), and (X) to (Z) in which the number of secondary amine structures (—NH—) contained in the molecule was 2 or more, the number of hydroxy groups was 4 or less, and a total number of hydroxy groups and secondary amine structures was 7 or less, the result of the friction coefficient increase time was A (excellent), which was a favorable result.

INDUSTRIAL APPLICABILITY

When the lubricant for a magnetic recording medium containing the fluorine-containing ether compound of the present invention is used, it is possible to form a lubricating layer that can realize excellent wear resistance even if the thickness is thin.

That is, according to the present invention, it is possible to provide a fluorine-containing ether compound which can form a lubricating layer having excellent wear resistance even if the thickness is thin and can be suitably used as a material for the lubricant for a magnetic recording medium.

REFERENCE SIGNS LIST

10 Magnetic recording medium

11 Substrate

12 Adhesive layer

13 Soft magnetic layer

14 First underlayer

15 Second underlayer

16 Magnetic layer

17 Protective layer

18 Lubricating layer

The invention claimed is:

1. A fluorine-containing ether compound represented by the following Formula (1):

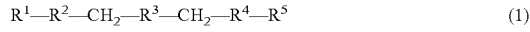 (1)

(in Formula (1), $R^3$ represents a perfluoropolyether chain; $R^1$ represents a terminal group bonded to $R^2$; $R^5$ represents a terminal group bonded to $R^4$; $R^1$ and $R^5$ each independently represent any of an alkyl group which may have a substituent, an organic group having a double bond or a triple bond, and a hydrogen atom; —R²—CH₂—R³ is represented by the following Formula (2); and R³—CH₂—R⁴— is represented by the following Formula (3); and a total of one or more secondary amine —NH— is contained in R² and R⁴):

-[A]-[B]—O—CH₂—R³         (2)

R³—CH₂—O—[C]-[D]-         (3)

(in Formula (2), [A] is represented by the following Formula (4), and [B] is represented by the following Formula (5); and in Formula (2), [A] and [B] may be interchanged), and (in Formula (3), [C] is represented by the following Formula (6), and [D] is represented by the following Formula (7); and in Formula (3), [C] and [D] may be interchanged):

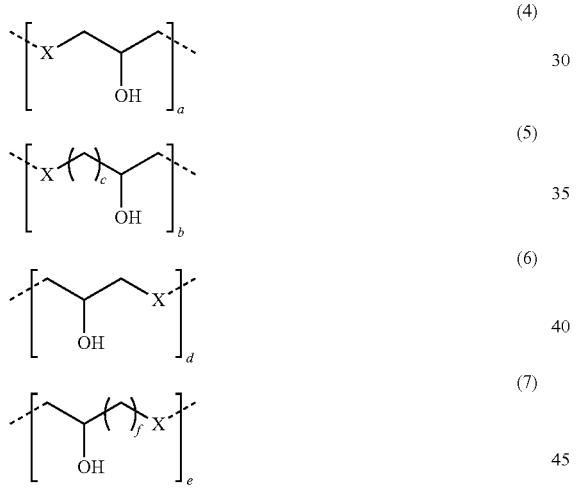

(a in Formula (4) and b in Formula (5) represent an integer of 0 to 2; c in Formula (5) represents an integer of 2 to 5; d in Formula (6) and e in Formula (7) represent an integer of 0 to 2; f in Formula (7) represents an integer of 2 to 5; at least one of b in Formula (5) and d in Formula (6) represents 1 or more; X represents any of O, NH, and CH₂; one or more of X's in Formulae (4) to (7) represent NH; and when X bonded to R¹ or R⁵ represents NH, R¹ or R⁵ represents either an alkyl group which may have a substituent or an organic group having a double bond or a triple bond).

2. The fluorine-containing ether compound according to claim 1, wherein the number of secondary amine structures contained in the molecule is 2 or more.

3. The fluorine-containing ether compound according to claim 1, wherein the number of hydroxy groups contained in the molecule is 4 or less.

4. The fluorine-containing ether compound according to claim 1, wherein a total number of secondary amine structures and hydroxy groups contained in the molecule is 7 or less.

5. The fluorine-containing ether compound according to claim 1, wherein, in the molecule thereof, the number of secondary amine structures is 2 or more, the number of hydroxy groups is 4 or less, and a total number of secondary amine structures and hydroxy groups is 7 or less.

6. The fluorine-containing ether compound according to claim 1, wherein, in Formula (1), $R^2$ represents any of the following Formulae (11-1) to (11-5):

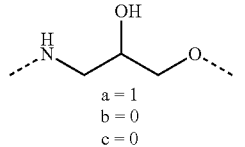
(11-1)

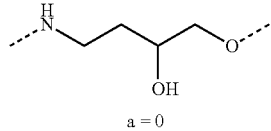
(11-2)

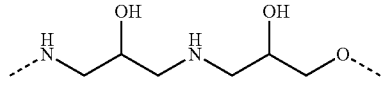
(11-3)

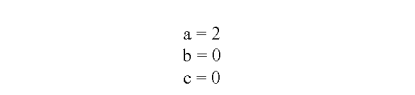
(11-4)

-continued (11-5)

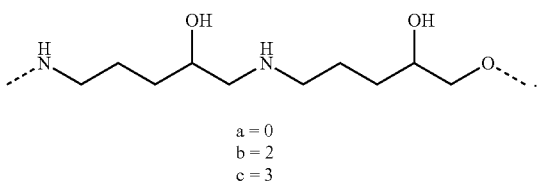

a = 0
b = 2
c = 3

7. The fluorine-containing ether compound according to claim 1, wherein the alkyl group which may have a substituent is an alkyl group having a hydroxy group and having 1 to 6 carbon atoms.

8. The fluorine-containing ether compound according to claim 1, wherein the organic group having a double bond or a triple bond is any one of an aromatic hydrocarbon-containing group, an aromatic heterocycle-containing group, an alkenyl group, and an alkynyl group.

9. The fluorine-containing ether compound according to claim 1, wherein, in Formula (1), $R^3$ represents any of the following Formulae (8) to (10):

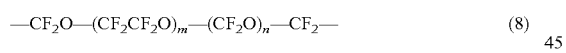           (8)

(in Formula (8), m and n indicate an average degree of polymerization, and each represents 0 to 30; where, m or n is 0.1 or more),

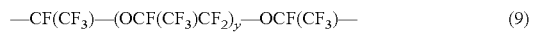           (9)

(in Formula (9), y indicates an average degree of polymerization, and represents 0.1 to 30), and

           (10)

(in Formula (10), z indicates an average degree of polymerization, and represents 0.1 to 30).

10. The fluorine-containing ether compound according to claim 1, wherein a sum of a in Formula (4) and b in Formula (5), and a sum of d in Formula (6) and e in Formula (7) are each 1 or more.

11. The fluorine-containing ether compound according to claim 1, wherein the compound represented by Formula (1) is any of compounds represented by the following Formulae (K) to (M), (S), and (T):

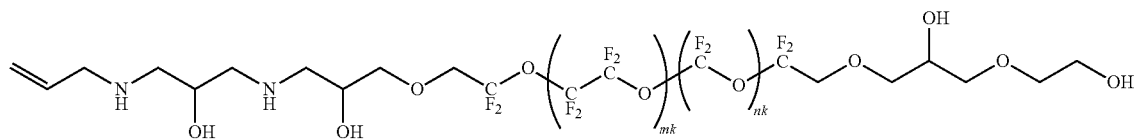
(K)
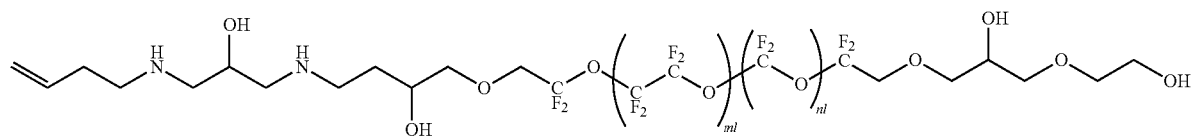
(L)
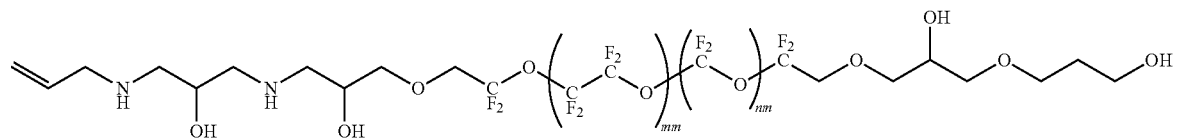
(M)
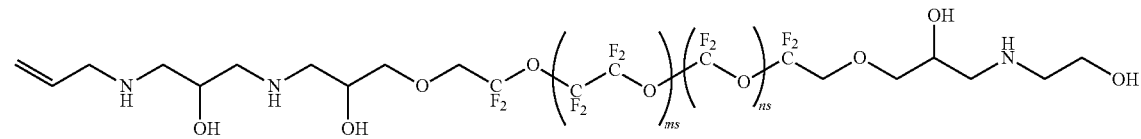
(S)
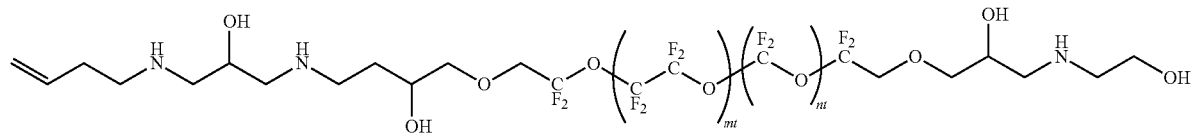
(T)

(in Formula (K), mk and nk indicate an average degree of polymerization, mk represents 1 to 30, and nk represents 0 to 30), (in Formula (L), ml and nl indicate an average degree of polymerization, ml represents 1 to 30, and nl represents 0 to 30), (in Formula (M), mm and nm indicate an average degree of polymerization, mm represents 1 to 30, and nm represents 0 to 30), (in Formula (S), ms and ns indicate an average degree of polymerization, ms represents 1 to 30, and ns represents 0 to 30), and (in Formula (T), mt and nt indicate an average degree of polymerization, mt represents 1 to 30, and nt represents 0 to 30).

12. The fluorine-containing ether compound according to claim 1, wherein the number-average molecular weight thereof is in a range of 500 to 10,000.

13. A lubricant for a magnetic recording medium, which contains the fluorine-containing ether compound according to claim 1.

14. A magnetic recording medium having at least a magnetic layer, a protective layer, and a lubricating layer sequentially provided on a substrate, wherein the lubricating layer contains the fluorine-containing ether compound according to claim 1.

15. The magnetic recording medium according to claim 14, wherein the average film thickness of the lubricating layer is 0.5 nm to 2.0 nm.

* * * * *